United States Patent
Hwang et al.

(10) Patent No.: US 11,160,840 B2
(45) Date of Patent: Nov. 2, 2021

(54) COMPOSITION FOR IMPROVEMENT OF MUSCLE FUNCTION CONTAINING 3,5-DICAFFEOYLQUINIC ACID OR CHRYSANTHEMUM EXTRACT

(71) Applicants: Industry-Academic Cooperation Foundation, Yonsei University, Seoul (KR); Cosmax NBT, Inc., Seoul (KR); Cosmax NS, Inc., Seoul (KR)

(72) Inventors: Jae Kwan Hwang, Seoul (KR); Jun Gon Yun, Seoul (KR); Mi Bo Kim, Seoul (KR); Chang Hee Kim, Seoul (KR); Joon Hyung Lee, Seoul (KR); Do Wan Kwon, Gyeongsangbuk-do (KR); Su Young Choi, Gyeonggi-do (KR); Jin Hak Kim, Seoul (KR); Ji Hwan Jang, Gyeonggi-do (KR); Jeong Ho Geum, Seoul (KR); Min Son Kweon, Seoul (KR)

(73) Assignees: Industry-Academic Cooperation Foundation, Yonsei University, Seoul (KR); Cosmax NBT, Inc., Seoul (KR); Cosmax NS, Inc., Seoul (KR)

( * ) Notice: Subject to any disclaimer, the term of this patent is extended or adjusted under 35 U.S.C. 154(b) by 0 days.

(21) Appl. No.: 16/474,528

(22) PCT Filed: Nov. 30, 2017

(86) PCT No.: PCT/KR2017/013879
§ 371 (c)(1),
(2) Date: Jun. 27, 2019

(87) PCT Pub. No.: WO2018/124508
PCT Pub. Date: Jul. 5, 2018

(65) Prior Publication Data
US 2020/0009208 A1  Jan. 9, 2020

(30) Foreign Application Priority Data
Dec. 30, 2016 (KR) ......... 10-2016-0183649

(51) Int. Cl.
| | |
|---|---|
| A61K 36/287 | (2006.01) |
| A23L 33/105 | (2016.01) |
| A61K 8/9789 | (2017.01) |
| A61K 8/37 | (2006.01) |
| A61K 31/216 | (2006.01) |

(52) U.S. Cl.
CPC .......... *A61K 36/287* (2013.01); *A23L 33/105* (2016.08); *A61K 8/37* (2013.01); *A61K 8/9789* (2017.08); *A61K 31/216* (2013.01)

(58) Field of Classification Search
None
See application file for complete search history.

(56) References Cited

U.S. PATENT DOCUMENTS

| | | | |
|---|---|---|---|
| 2011/0054022 A1* | 3/2011 | Poessel | C07C 51/42 514/533 |
| 2012/0010285 A1 | 1/2012 | Takatoshi et al. | |
| 2015/0209399 A1* | 7/2015 | Fields | A61K 31/216 424/769 |
| 2016/0151436 A1* | 6/2016 | Squires | A61K 36/28 424/400 |
| 2019/0030200 A1* | 1/2019 | Wang | A61L 9/01 |

FOREIGN PATENT DOCUMENTS

| | | |
|---|---|---|
| CN | 101185668 | 5/2008 |
| CN | 104324282 | 2/2015 |
| CN | 104546819 | * 4/2015 |
| CN | 105012908 | 11/2015 |
| CN | 105395940 | 3/2016 |
| CN | 105878644 | * 8/2016 |

(Continued)

OTHER PUBLICATIONS

Kumar, A. et al. Secondary Metabolites of *Chrysanthemum* Genus and Their Biological Activities. Current Science 89(9)1489-1501, Nov. 2005. (Year: 2005).*
Flann et al., "Muscle damage and muscle remodeling: no pain, no gain?" The Journal of Experimental Biology (2011) 214, 674-679.
Haouas et al., "Insecticidal Activity of Flower and Leaf Extracts from *Chrysanthemum* Species Against Tribolium confusum," Tunisian Journal of Plant Protection 3(2): 87-93, 2008.
Jang et al., "Antimicrobial Activity of Plants in the Genus *Chrysanthemum*," Korean Journal of Agricultural Chemistry, 39(4) 315-319, 1996 (Including English abstract).

(Continued)

*Primary Examiner* — Ralph J Gitomer
(74) *Attorney, Agent, or Firm* — Morrison Foerster LLP

(57) ABSTRACT

The present invention relates to a composition for preventing or treating a muscle disorder, which includes a chrysanthemum extract or 3,5-dicaffeoylquinic acid as an active ingredient, and specifically, it may be used to reduce mRNA expression of atrogin-1 and MuRF1, which are main biomarkers involved in muscle protein degradation and increase mRNA expression of the mTOR protein, which is a main biomarker involved in muscle protein formation, and myogenin and MyoD, which are biomarkers related to muscle differentiation, thereby reducing muscle loss, and thus the chrysanthemum extract or 3,5-dicaffeoylquinic acid can be used in prevention and treatment of a muscle disorder, or improvement in muscle function. In addition, the chrysanthemum extract or 3,5-dicaffeoylquinic acid increases the activity of SIRT1 and PGC-1α, which are the main biomarkers involved in exercise performance, thereby excellently enhancing exercise performance. In addition, the present invention is a natural substance and may be safely used without a side effect, and therefore may be used as a medication, food or a cosmetic.

5 Claims, 14 Drawing Sheets

Specification includes a Sequence Listing.

(56) References Cited

FOREIGN PATENT DOCUMENTS

| JP | 2006-265231 | 10/2006 | |
|---|---|---|---|
| JP | 2015-086165 | 5/2015 | |
| KR | 10-2012-0092763 | 8/2012 | |
| KR | 10-2013-0000664 | 1/2013 | |
| KR | 10-2014-0000767 | 1/2014 | |
| WO | WO 2010/106798 | * | 1/2010 |

OTHER PUBLICATIONS

Sun et al., "Flavonoids and volatiles in *Chrysanthemum morifolium* Ramat flower from Tongxiang County in China," African Journal of Biotechnology, 9(25):3817-3821, 2010.

Wu et al., "Analysis of chemical composition of Chrysanthemum indicum flowers by GC/MS and HPLC," J. Med. Plant Res., 4(5): 421-426, 2010.

Beninger et al., "A Flavanone and Two Phenolic Acids From Chrysanthemum morifolium With Phytotoxic and Insect Growth Regulating Activity," Journal of Chemical Ecology (2004) 30(3):589-606.

Clifford et al., "Profiling the Chlorogenic Acids and Other Caffeic Acid Derivatives of Herbal Chrysanthemum by LC-MS", J. Agric. Food Chem (2007) 55:929-936.

Hong et al., "Anxiolytic-Like Effects of Chrysanthemum indicum Aqueous Extract in Mice: Possible Involvement of GABAA Receptors and 5-HT1A Receptors," Biomol Ther (2012) 20(4):413-417.

Kim et al., "Chrysanthemum morifolium Ramat (CM) extract protects human neuroblastoma SH-SY5Y cells against MPP+-induced cytotoxicity," Journal of Ethnopharmacology (2009) 126:447-454.

Kim et al., "Neuroprotective Effects of 3,5-Dicaffeoylquinic Acid on Hydrogen Peroxide-induced Cell Death in SH-SY5Y Cells," Phytother Res (2005) 19:243-245.

Lin et al., "Antioxidant Action of a Chrysanthemum morifolium Extract Protects Rat Brain Against Ischemia and Reperfusion Injury," J Med Food (2010) 13(2):306-311.

Qiao et al., "Effects of Dietary Dioscorea opposita and Chrysanthemum morifolium on Muscle Composition in Common Carp *Cyrinus carpio*," Fisheries Science (2010) 5:249-254.

Cheeti et al., "Autoimmune Myopathies," retrieved from https://www.ncbi.nlm.nih.gov/books/NBK532860/ on Dec. 29, 2020.

Foletta et al., "The role and regulation of MAFbx/atrogin-1 and MuRF1 in skeletal muscle atrophy," Eur J Physiol (2011) 461:325-335.

Mitsui et al., "Chronic corticosteroid administration causes mitochondrial dysfunction in skeletal muscle," J Neurol (2002) 249:1004-1009.

Moreira et al. "Prevalence of sarcopenia and its associated factors: the impact of muscle mass, gait speed, and handgrip strength reference values on reported frequencies," Clinics (2015) 74:e477.

Park et al., "Hypopigmentation and subcutaneous fat, muscle atrophy after local corticosteroid injection," Korean J Anesthesiol (2013) 65(6 Suppl):S59-S61.

Wackerhage, "Sarcopenia: Causes and Treatments," Dtsch Z Sportmed (2017) 68:178-184.

2021 ICD-10-CM Diagnosis Code M33.2, Polymyositis, available at https://www.icd10data.eom/ICD10CM/Codes/M00-M99/M30-M36/M33-/M33.2, retrieved Dec. 29, 2020, 2 pages.

2021 ICD-10-CM Diagnosis Code M62.84, Sarcopenia, available at https://www.ncbi.nlm.nih.gov/books/NBK532860/, retrieved Dec. 29, 2020, 2 pages.

* cited by examiner

COMPOSITION FOR IMPROVEMENT OF MUSCLE FUNCTION CONTAINING 3,5-DICAFFEOYLQUINIC ACID OR CHRYSANTHEMUM EXTRACT

SEQUENCE LISTING

The present application is being filed along with a Sequence Listing in electronic format. The Sequence Listing is provided as a file entitled 717572000200SeqList.TXT, created Sep. 9, 2019 which is 3,037 bytes in size. The information in the electronic format of the Sequence Listing is incorporated by reference in its entirety.

CROSS REFERENCE TO RELATED APPLICATIONS

This application is a national stage application under 35 U.S.C. § 371 of International Application No. PCT/KR2017/013879, filed internationally on Nov. 30, 2017, which claims priority to and the benefit of Korean Patent Application No. 10-2016-0183649, filed on Dec. 30, 2016, the disclosures of which are incorporated herein by reference in their entirety.

TECHNICAL FIELD

The present invention relates to a composition for preventing, improving or treating a muscle disorder or improving muscle function, and more particularly, to a composition for preventing, improving or treating a muscle disorder or improving muscle function, which includes 3,5-dicaffeoylquinic acid or a chrysanthemum extract.

BACKGROUND ART

Over the past 50 to 100 years, the decline in human physical activity has been known to be associated with an increased incidence of metabolic diseases such as type 2 diabetes, obesity, cardiovascular diseases, etc. The lack of physical activity is the fourth leading cause of death, as reported by the World Health Organization. Due to this phenomenon, organizations such as the World Health Organization, the American Heart Association and the British Heart Foundation recommend a minimum of 30 minutes of aerobic exercise for at least five days a week. In fact, it has been reported that exercise reduces the incidence of diabetes, obesity, breast cancer and colon cancer, and has a high therapeutic effect on depression (Br. J. Pharmacol., 170: 1153-1166, 2013; Am. J. Cardiol., 110: 58B-68B, 2012).

Skeletal muscle fibers are generally classified as type 1 (oxidative/slow) and type 2 (glycolytic/fast) fibers, and muscle fibers exhibit significant differences in shrinkage, metabolism and susceptibility to fatigue. The type 1 fiber has a large number of mitochondria and mainly uses an oxidative metabolism for energy generation, and therefore stably provides ATP for a long time to withstand fatigue. Therefore, muscle wasting does not occur in the skeletal muscles with a lot of type 1 fibers (Muscle Nerve, 31: 339-348, 2005). Type 2 fibers have low contents of mitochondria and oxidases and are dependent on a glycolytic metabolism as a main energy source such that the fibers become easily tired.

Peroxisome Proliferator Activated Receptor δ (PPARδ) is a main transcription regulatory factor which is highly present in a skeletal muscle, particularly, type 1 fiber (10 fold of PPARα, and 50 fold of PPARγ), activates enzymes involved in β-oxidation of a long-chain fatty acid to burn fats in adipose cells (Cell, 113: 159-170, 2003), and is the first transcription factor which promotes type 1 fibrosis. Such PPARδ is known to be involved in a complicated pathway for regulating mitochondrial biogenesis upon activation and promoting exercise performance and resistance to obesity (PLoS Biol., 2: 1532-1539, 2004). Therefore, type 1 fibers generated adaptively through exercise are known to be resistant to fatigue. However, it has been reported that the same effects have been exhibited even when overexpression of PPARδ is artificially overexpressed in muscles without exercise. As a result of artificially overexpression of PPARδ in mouse muscles, mitochondrial biogenesis was increased, and the expression of fatty acid beta-oxidase and an increase in type 1 muscle fibers led to 67% and 92% increases in time and a distance for continuous running, compared with normal rats, respectively (PLoS Biol., 2: 1532-1539, 2004). Therefore, when PPARδ is activated, the form of a muscle fiber may be changed, resulting in enhancement of exercise performance.

As one of the representative methods for enhancing exercise performance by promoting energy consumption, there is a method of producing ATP energy by increasing fatty acid oxidation by mitochondria. It has been discovered that the number and ability of mitochondria involved in this method are regulated by a peroxisome proliferator-activated receptor-gamma coactivator 1 alpha (PGC-1a) coactivator, and PGC-1α activity is regulated by sirtuin 1 (SIRT1) (EMBO. J., 26:1913-1923, 2007, Cell Metab., 1: 361-370, 2005).

Muscle atrophy occurs by a gradual decrease in muscle mass, and refers to muscular weakness and degeneration (Cell, 119(7): 907-910, 2004). Muscle atrophy is promoted by inactivity, oxidative stress or chronic inflammation, and weakens muscle function and exercise performance (Clin. Nutr., 26(5): 524-534, 2007). The most important factor determining muscle function is muscle mass, which is maintained by a balance of protein synthesis and degradation. Muscle atrophy occurs when protein degradation happens more than protein synthesis (Int. J. Biochem. Cell Biol., 37(10): 1985-1996, 2005).

When a transcription factor, forkhead box (FoxO), migrates into the nucleus from the cytoplasm, expression of E3 ubiquitin ligase factor atrogin-1 and muscle RING-finger protein-1 (MuRF-1), which are involved in protein degradation, is increased (Dis. Model. Mech., 6: 25-39, 2013). When their expression levels are increased, protein degradation in muscles is promoted, thereby reducing muscle mass. Therefore, the inhibition of atrogin-1 expression reduces a loss of the amount of muscular proteins to maintain normal muscle function.

The scientific name of chrysanthemum is *Chrysanthemum morifolium* Ramat., which is generally used for ornamental plants, for making chrysanthemum tea using flower thereof, and for a salad, soup or alcohol (Edible Medicinal and Non-Medicinal Plants, 7: 250-269, 2012). It has been reported that chrysanthemum has an antioxidative effect (Afr. J. Biotechnol., 10(82): 19197-19202, 2011), an anti-tuberculosis action (Biol. Pharm. Bull., 28(1):158-160, 2005), and an anticancer effect (Cancer Lett., 177: 7-12, 2002).

It has been reported that 3,5-dicaffeoylquinic acid contained in chrysanthemum has an antiviral effect (Biochem, Pharmacol., 49: 1165-1170, 1995), an antiallergic effect (J. Agric. Food Chem., 54: 2915-2920, 2006), and a neuroprotective effect (Phytother. Res., 19: 243-245, 2005).

However, an exercise performance-enhancing effect of chrysanthemum and 3,5-dicaffeoylquinic acid or effects of preventing and improving a muscle disorder have not been known yet.

DISCLOSURE

Technical Problem

The present invention is directed to providing a pharmaceutical composition for preventing or treating a muscle disorder, which includes a chrysanthemum extract as an active ingredient.

The present invention is also directed to providing a pharmaceutical composition for preventing or treating a muscle disorder, which includes 3,5-dicaffeoylquinic acid of Formula 1 as an active ingredient:

[Formula 1]

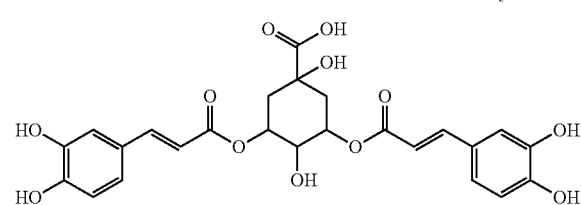

The present invention is also directed to providing a food composition for preventing or improving a muscle disorder, or improving muscle function, which contains a chrysanthemum extract as an active ingredient.

The present invention is also directed to providing a food composition for preventing or improving a muscle disorder, or improving muscle function, which contains 3,5-dicaffeoylquinic acid of Formula 1 as an active ingredient.

The present invention is also directed to providing a cosmetic composition for preventing or improving a muscle disorder, or improving muscle function, which contains a chrysanthemum extract as an active ingredient.

The present invention is also directed to providing a cosmetic composition for preventing or improving a muscle disorder, or improving muscle function, which contains a compound of Formula 1 as an active ingredient.

The present invention is also directed to providing a pharmaceutical composition for enhancing exercise performance, which contains a chrysanthemum extract as an active ingredient.

The present invention is also directed to providing a pharmaceutical composition for enhancing exercise performance, which contains 3,5-dicaffeoylquinic acid of Formula 1 as an active ingredient:

[Formula 1]

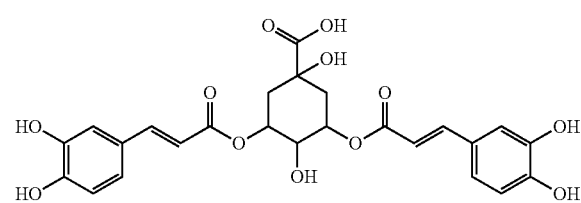

The present invention is also directed to providing a food composition for enhancing exercise performance, which contains a chrysanthemum extract as an active ingredient.

The present invention is also directed to providing a food composition for enhancing exercise performance, which contains 3,5-dicaffeoylquinic acid of Formula 1 as an active ingredient.

The present invention is also directed to providing a cosmetic composition for enhancing exercise performance, which contains a chrysanthemum extract as an active ingredient.

The present invention is also directed to providing a cosmetic composition for enhancing exercise performance, which contains 3,5-dicaffeoylquinic acid of Formula 1 as an active ingredient.

However, technical problems to be solved by the present invention are not limited to the above-mentioned problems, and other problems which are not mentioned can be clearly understood by those of ordinary skill in the art from the following descriptions.

Technical Solution

In one aspect, the present invention provides a pharmaceutical composition for preventing or treating a muscle disorder, which contains a chrysanthemum extract as an active ingredient.

In another aspect, the present invention provides a pharmaceutical composition for preventing or treating a muscle disorder, which contains 3,5-dicaffeoylquinic acid of Formula 1 or a pharmaceutically acceptable salt thereof as an active ingredient:

[Formula 1]

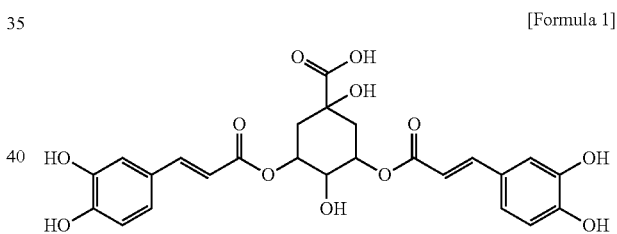

In still another aspect, the present invention provides a food composition for preventing or improving a muscle disorder or improving muscle function, which contains a chrysanthemum extract, 3,5-dicaffeoylquinic acid of Formula 1 or a pharmaceutically acceptable salt thereof as an active ingredient.

In yet another aspect, the present invention provides a cosmetic composition for preventing or improving a muscle disorder or improving muscle function, which contains a chrysanthemum extract, 3,5-dicaffeoylquinic acid of Formula 1 or a pharmaceutically acceptable salt thereof as an active ingredient.

The chrysanthemum extract may include 3,5-dicaffeoylquinic acid of Formula 1 as an active ingredient.

The chrysanthemum extract may be obtained by extracting chrysanthemum using water, an organic solvent having 1 to 6 carbon atoms, or a mixture thereof as a solvent.

The chrysanthemum extract may be obtained by extracting chrysanthemum through subcritical fluid extraction, supercritical fluid extraction, or high-pressure extraction.

As the 3,5-dicaffeoylquinic acid, a compound isolated from the chrysanthemum extract, or a synthetic compound or a commercially available compound may be used.

The muscle disorder may be a muscle disorder caused by a decrease in muscle function, muscle wasting or muscle degeneration.

The muscle disorder may be one or more selected from the group consisting of atony, muscular atrophy, muscular dystrophy, myasthenia, cachexia and sarcopenia.

The composition may promote formation of muscle fibers.

In addition, the present invention provides a pharmaceutical composition for enhancing exercise performance, which contains a chrysanthemum extract, 3,5-dicaffeoylquinic acid or a pharmaceutically acceptable salt thereof as an active ingredient.

In addition, the present invention provides a food composition for enhancing exercise performance, which contains a chrysanthemum extract, 3,5-dicaffeoylquinic acid or a pharmaceutically acceptable salt thereof as an active ingredient.

In addition, the present invention provides a cosmetic composition for enhancing exercise performance, which contains a chrysanthemum extract, 3,5-dicaffeoylquinic acid or a pharmaceutically acceptable salt thereof as an active ingredient.

The composition may have effects of increasing exercise endurance, reinforcing muscle strength, enhancing balance, and/or enhancing exercise adaptation.

The composition may increase the oxidative metabolic function of mitochondria.

The composition may promote formation of muscle fibers.

Advantageous Effects

The present invention relates to a composition for preventing and treating a muscle disorder containing a chrysanthemum extract or 3,5-dicaffeoylquinic acid as active ingredients, wherein the chrysanthemum extract or 3,5-dicaffeoylquinic acid can reduce mRNA expression of atrogin-1 and MuRF1, which are main biomarkers involved in muscle protein degradation and increase mRNA expression of the mTOR protein, which is a main biomarker involved in muscle protein formation, and myogenin and MyoD, which are biomarkers related to muscle differentiation, thereby reducing muscle loss, and thus the chrysanthemum extract or 3,5-dicaffeoylquinic acid can be used in prevention and treatment of a muscle disorder, or improvement in muscle function. In addition, the chrysanthemum extract or 3,5-dicaffeoylquinic acid increases the activity of PPARδ and PGC-1α, which are the main biomarkers involved in exercise performance, thereby excellently enhancing exercise performance.

MODES OF THE INVENTION

Figure 1:
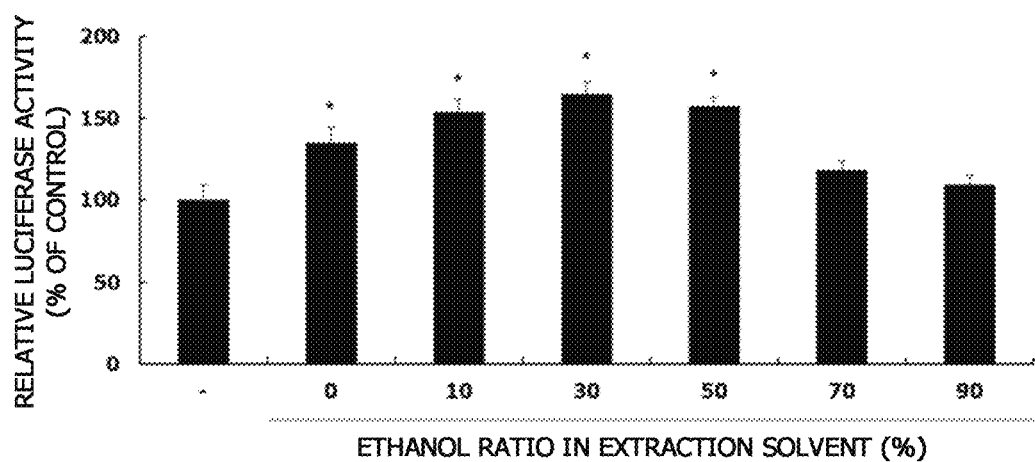
FIG. 1 shows a result of measuring the activity of a PPARδ ligand-binding domain according to treatment with a chrysanthemum optimized hot water extract and 10%, 30%, 50%, 70% and 90% ethanol extracts.

The inventors had discovered that a chrysanthemum extract and 3,5-dicaffeoylquinic acid have an activity of forming muscle and an activity of enhancing exercise performance, and therefore the present invention was completed.

The term "muscle" used herein encompasses to a tendon, a muscle and a cord, and the "muscle function" used herein refers to an ability of generating power by muscle contraction, and includes muscular strength, which is the ability of muscles to exert maximum contraction to overcome resistance, muscle endurance, which is the ability of muscles to show how long or how many contractions and relaxations are repeated with a given weight, and agility, which is the ability of exerting strong power within short time. Such muscle functions are governed by the liver and proportional to muscle mass, and the "improvement in muscle function" refers to more enhancement in muscle function.

The term "exercise performance" used herein refer to a degree of rapidly, intensively, accurately, longer and smoothly performing an action when body actions shown in normal life or sports are explicitly divided into running, hopping, throwing and swimming, and is defined by parameters such as muscular strength, agility and endurance, and the "enhancement in exercise performance" refers to improvement or enhancement in exercise performance.

Hereinafter, the present invention will be described in detail.

Pharmaceutical Composition for Preventing or Treating Muscle Disorder

The present invention provides a pharmaceutical composition for preventing or treating a muscle disorder containing a chrysanthemum extract as an active ingredient.

The chrysanthemum extract may include 3,5-dicaffeoylquinic acid of Formula 1 below as an active ingredient.

The chrysanthemum may be a plant of the genus *Chrysanthemum* in the family Asteraceae, and is called *Chrysanthemum morifolium*, but the present invention is not limited thereto. Here, the leaves, stems, flowers, root, skin or fruit of the chrysanthemum, or a mixture thereof may be subjected to extraction.

Specifically, the chrysanthemum extract may be extracted using water, an organic solvent having 1 to 4 carbon atoms or a mixture thereof as a solvent. Here, the organic solvent may be one or more selected from the group consisting of a C1 to C4 lower alcohol, acetone, ether, benzene, chloroform, ethyl acetate, methylene chloride, hexane, cyclohexane and petroleum ether, but the present invention is not limited.

In addition, the lower alcohol used in extraction of the chrysanthemum is more preferably ethanol or methanol, and most preferably ethanol. Specifically, in the case of using ethanol as a solvent for extraction of the chrysanthemum, when a 10 to 95% ethanol aqueous solution is used, an effect of enhancing exercise performance and an activity to inhibit muscular protein degradation may be more significantly exhibited in preparation of a chrysanthemum extract. More specifically, when the chrysanthemum extract is prepared, a 30 to 95% ethanol aqueous solution is preferably used as a solvent, but the present invention is not limited thereto.

In extraction, dry chrysanthemum may be ground, and then water, an alcohol or a mixture thereof is preferably added 2 to 20 fold, and more preferably, added 3 to 10 fold, the weight of the ground chrysanthemum, but the present invention is not limited thereto. An extraction temperature is preferably 20 to 100° C., and more preferably 60 to 100° C., but the present invention is not limited thereto. The extraction time is preferably 1 to 10 hours, and more preferably 2 to 5 hours, but the present invention is not limited thereto. An extraction method can be any one of cold extraction, ultrasonic extraction and reflux cooling extraction, and the reflux cooling extraction is preferably used, but the present invention is not limited thereto. The number of extraction cycles is preferably 1 to 5 times, and more preferably 2 or 3 times, but the present invention is not limited thereto.

In addition, the chrysanthemum extract may be attained by ultra-high pressure extraction, subcritical fluid extraction or supercritical fluid extraction.

The present invention may also provide a pharmaceutical composition for preventing or treating a muscle disorder, which contains a compound of Formula 1 below or a pharmaceutically acceptable salt thereof as an active ingredient:

[Formula 1]

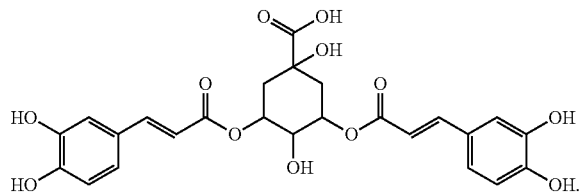

The compound of Formula 1 is called 3,5-dicaffeoylquinic acid.

The structural name of the 3,5-dicaffeoylquinic acid is (3R,5R)-3,5-bis[[(E)-3-(3,4-dihydroxyphenyl)prop-2-enoyl]oxy]-1,4-dihydroxycyclohexane-1-carboxylic acid, and corresponds to CAS No. 89919-62-0.

As the compound of Formula 1, a compound isolated or synthesized from a chrysanthemum extract or may be a commercially-available compound may be used.

The composition according to the present invention may inhibit muscle loss. Specifically, as mRNA expression of atrogin-1 and MuRF1, which are the main biomarkers involved in muscle protein degradation, may be decreased, and mRNA expression of the mTOR protein, which is the main biomarker involved in formation of a muscle protein and myogenin and MyoD, which are biomarkers related to muscle differentiation, may be increased, the composition may be used in prevention or treatment of a muscle disorder.

The muscle disorder of the present invention may be a muscle disorder caused by a decrease in muscle function, muscle wasting or muscle degeneration, which is a disease which has been reported in the art, and specifically, any one or more selected from the group consisting of atony, muscular atrophy, muscular dystrophy, muscle degeneration, myasthenia, cachexia and sarcopenia, but the present invention is not limited thereto.

The muscle wasting or degeneration is caused by an innate factor, an acquired factor, aging or the like, and the muscle wasting contributes to gradual loss of muscle mass, and weakening and degeneration of a muscle, particularly, a skeletal muscle, a voluntary muscle or a heart muscle.

In the composition of the present invention, a content of the chrysanthemum extract may be 1 to 100 µg/mL, and a content of the 3,5-dicaffeoylquinic acid may be 1 to 100 µM, but the present invention is not limited thereto.

The pharmaceutical composition for preventing or treating a muscle disorder according to the present invention may be formulated in oral preparations such as a powder, a granule, a capsule, a suspension, an emulsion, a syrup and an aerosol, a preparation for external use, a suppository and a sterilized injection according to a conventional method, and may include a suitable carrier, excipient or diluent, which is conventionally used in preparation of a pharmaceutical composition for formulation.

As the carrier, excipient or diluent, various compounds including lactose, dextrose, sucrose, sorbitol, mannitol, xylitol, erythritol, maltitol, starch, acacia gum, alginate, gelatin, calcium phosphate, calcium silicate, cellulose, methyl cellulose, microcrystalline cellulose, polyvinyl pyrrolidone, water, methylhydroxybenzoate, propylhydroxybenzoate, talc, magnesium stearate and mineral oil, or a mixture thereof may be used.

The pharmaceutical composition may be prepared with a diluent or excipient such as a filler, a thickening agent, a binder, a wetting agent, a disintegrant or a surfactant, which is generally used in the preparation.

A solid preparation for oral administration may be prepared by mixing at least one or more excipients such as starch, calcium borate, sucrose, lactose, and gelatin with the chrysanthemum extract. In addition, other than a simple excipient, lubricants such as magnesium stearate, talc, etc. may also be used.

A liquid preparation for oral administration may be a suspension, a liquid for internal use, an emulsion, or a syrup, and may include various excipients, for example, a wetting agent, a sweetening agent, a flavoring agent, a preservative, etc., other than a simple diluent frequently used, for example, water or liquid paraffin.

Examples of preparations for non-oral administration may include a sterilized aqueous solution, a non-aqueous solvent, a suspension, an emulsion, a lyophilizing agent and a suppository. As the non-aqueous solvent or suspension, propylene glycol, polyethylene glycol, a vegetable oil such as olive oil, or an injectable ester such as ethyl oleate may be used. As a suppository base, Witepsol, Tween 61, cacao butter, laurin fat, or glycerogelatin may be used.

A preferable dose of the pharmaceutical composition for preventing or treating a muscle disorder according to the present invention may be determined by a patient's condition and body weight, severity of a disease, a drug type, an administration route and a duration, and may be suitably selected by those of ordinary skill in the art. However, for a preferable effect, the pharmaceutical composition for preventing or treating a muscle disorder according to the present invention may be administered daily at 0.0001 to 2,000 mg/kg, and preferably 0.001 to 2,000 mg/kg. The pharmaceutical composition for preventing or treating a muscle disorder according to the present invention may be administered once or in divided doses per day. However, the scope of the present invention is not limited by the dose.

The pharmaceutical composition for preventing or treating a muscle disorder according to the present invention may be administered to mammals such as rats, mice, livestock and humans via various routes. The administration may be performed orally, intravenously, intramuscularly, subcutaneously, intrathecally, or intracerebroventricularly.

Health Functional Food Composition for Preventing or Improving Muscle Disorder

The present invention provides a health functional food composition for preventing or improving a muscle disorder, which contains a chrysanthemum extract as an active ingredient.

In addition, the present invention provides a health functional food composition for preventing or improving a muscle disorder, which contains a compound of Formula 1 or a pharmaceutically acceptable salt thereof as an active ingredient:

The chrysanthemum may be a plant of the genus *Chrysanthemum* in the family Asteraceae, and is called *Chrysanthemum morifolium*, and the chrysanthemum has been described above. As the 3,5-dicaffeoylquinic acid of Formula 1, a compound isolated or synthesized from a chrysanthemum extract or a commercially-available compound may be used, and details have been described above.

Food Composition for Improving Muscle Function

The present invention provides a health functional food composition for preventing or improving a muscle disorder, which contains a chrysanthemum extract as an active ingredient.

The present invention also provides a food composition for preventing a muscle disorder or improving muscle function, which contains 3,5-dicaffeoylquinic acid of Formula 1 or a pharmaceutically acceptable salt thereof as an active ingredient.

The chrysanthemum may be a plant of the genus *Chrysanthemum* in the family Asteraceae, and is called *Chrysanthemum morifolium*, and the chrysanthemum has been described above.

As the 3,5-dicaffeoylquinic acid of Formula 1, a compound isolated or synthesized from a chrysanthemum extract or a commercially-available compound may be used, and details have been described above.

In the food composition for improving muscle function according to the present invention, when the chrysanthemum extract or 3,5-dicaffeoylquinic acid is used as an additive for health functional food, it may be added alone or in combination with other food or food components, and may be suitably used according to a conventional method. A mixing amount of the active ingredient may be suitably determined according to a purpose of use, for example, for prevention, health care or treatment.

A health functional food can be produced in the form of common food or beverage, as well as a powder, a granule, a pill, a tablet or a capsule.

There is no particular limitation to a type of the food, and examples of food to which the material can be added may include meat, sausage, bread, chocolate, candy, snacks, confectionaries, pizza, ramen, other noodles, gums, dairy products including ice cream, soups, beverages, tea, drinks, alcoholic beverages and vitamin complexes, and may include all types of food in a conventional meaning.

Generally, in preparation of food or a beverage, the chrysanthemum extract or 3,5-dicaffeoylquinic acid may be added at 15 parts by weight or less, and preferably, 10 parts by weight or less with respect to 100 parts by weight of the raw materials. However, in the case of long-term intake of the food for health and sanitary or health control, the amount may be in the range or less, and since the present invention uses a fraction obtained from a natural substance and thus there is no problem in stability, the food may be used in an amount higher than the above range.

A beverage among the health functional food according to the present invention may contain various flavoring agents or a natural carbohydrate as an additional component like a conventional beverage. The above-described natural carbohydrate may be a monosaccharide such as glucose or fructose, a disaccharide such as maltose or sucrose, a polysaccharide such as dextrin or cyclodextrin, or a sugar alcohol such as xylitol, sorbitol or erythritol. As a sweetening agent, a natural sweetening agent such as thaumatin or a stevia extract, or a synthetic sweetening agent such as saccharine or aspartame may be used. A ratio of the natural carbohydrate may be approximately 0.01 to 0.04 g, and preferably, approximately 0.02 to 0.03 g, per 100 mL of the beverage according to the present invention.

Other than the above-mentioned components, the health functional food for improving muscle function according to the present invention may contain various nutrients, vitamins, electrolytes, flavoring agents, coloring agents, pectic acid and salts thereof, alginic acid and salts thereof, organic acids, a protective colloid thickening agent, a pH adjuster, a stabilizer, a preservative, glycerin, alcohol, and a carbonating agent used in carbonated drinks. Other than these, the composition for improving muscle function may contain flesh for producing natural fruit juice, fruit drinks and vegetable drinks. Such components may be used alone or in combination. A ratio of the additive is not limited, but is generally selected in a range of 0.01 to 0.1 part by weight with respect to 100 parts by weight of the health functional food of the present invention.

Cosmetic Composition for Improving Muscle Function

The present invention provides a cosmetic composition for improving muscle function, which contains a chrysanthemum extract as an active ingredient.

In addition, the present invention provides a cosmetic composition for improving muscle function, which contains 3,5-dicaffeoylquinic acid of Formula 1 or a pharmaceutically acceptable salt thereof as an active ingredient.

The chrysanthemum may be a plant of the genus *Chrysanthemum* in the family Asteraceae, and is called *Chrysanthemum morifolium*, and the chrysanthemum has been described above.

As the 3,5-dicaffeoylquinic acid of Formula 1, a compound isolated or synthesized from a chrysanthemum extract or a commercially-available compound may be used, and details have been described above.

The cosmetic composition of the present invention may contain a chrysanthemum extract or 3,5-dicaffeoylquinic acid as an active ingredient, and also include a dermatologically acceptable excipient, and thus can be prepared in the form of a composition for basic cosmetics (toner, essence, cleanser such as cleansing foam or cleansing water, pack, and body oil), a composition for color cosmetics (foundation, lipstick, mascara, and makeup base), a composition for hair products (shampoo, rinse, hair conditioner, and hair gel) and soap.

As the excipient, an emollient, a skin permeation enhancer, a colorant, fragrance, an emulsifier, a thickener or a solvent may be included, but the present invention is not limited thereto. In addition, a flavor, a colorant, an antibacterial agent, an antioxidant, a preservative and a moisturizer may be further included, and for improvement in physical properties, a thickening agent, inorganic salts, and synthetic polymer materials may be included. For example, when a cleanser or soap are prepared using the cosmetic composition of the present invention, it may be easily prepared by adding the chrysanthemum extract or 3,5-dicaffeoylquinic acid to a conventional cleanser or soap base. A cream may be prepared by adding the chrysanthemum extract, 3,5-dicaffeoylquinic acid or a salt thereof to a common oil-in-water (OW) cream base. Here, in addition to a fragrance, a chelating agent, a colorant, an antioxidant, a preservative, etc., a synthetic or natural substance such as a protein, a mineral or a vitamin may be further added to improve physical properties. A content of the chrysanthemum extract or 3,5-dicaffeoylquinic acid contained in the cosmetic composition of the present invention is, but is not limited to, preferably 0.001 to 10 wt %, and more preferably 0.01 to 5 wt %, with respect to the total weight of the composition. When the content is less than 0.001 wt %, a desired antiaging or wrinkle-improving effect may not be expected, and when the content is more than 10 wt %, there may be difficulty in stability or formulation.

Pharmaceutical Composition for Improving Exercise Performance

The present invention provides a pharmaceutical composition for improving exercise performance, which contains a chrysanthemum extract as an active ingredient.

The present invention also provides a pharmaceutical composition for improving exercise performance, which contains 3,5-dicaffeoylquinic acid of Formula 1 or a pharmaceutically acceptable salt thereof.

The chrysanthemum may be a plant of the genus *Chrysanthemum* in the family Asteraceae, and is called *Chrysanthemum morifolium*, and the chrysanthemum has been described above.

As the 3,5-dicaffeoylquinic acid of Formula 1, a compound isolated or synthesized from a chrysanthemum extract or a commercially-available compound may be used, and details have been described above.

The composition may increase the oxidative metabolic function of mitochondria, and specifically, the chrysanthemum extract or 3,5-dicaffeoylquinic acid of the present invention may improve exercise performance by significantly increasing SIRT1 and PGC-1α expression levels in muscle cells.

In addition, the composition may promote formation of muscle fibers, and specifically, the chrysanthemum extract of the present invention may improve exercise performance by significantly increasing PPARδ activity.

In addition, the composition may prevent or treat any one or more diseases selected from the group consisting of a degenerative disease, mitochondrial dysfunction, a decrease in endurance, a decrease in agility, lethargy, muscle disuse and depression as the enhancement in exercise performance is induced.

Food Composition for Improving Exercise Performance

The present invention provides a food composition for improving exercise performance, which contains a chrysanthemum extract as an active ingredient.

In addition, the present invention provides a food composition for improving exercise performance, which contains 3,5-dicaffeoylquinic acid of Formula 1 or a pharmaceutically acceptable salt thereof as an active ingredient.

The chrysanthemum may be a plant of the genus *Chrysanthemum* in the family Asteraceae, and is called *Chrysanthemum morifolium*, and the chrysanthemum has been described above.

As the 3,5-dicaffeoylquinic acid of Formula 1, a compound isolated or synthesized from the chrysanthemum extract or a commercially available compound may be used, and the 3,5-dicaffeoylquinic acid may be the same as described above.

Cosmetic Composition for Enhancing Exercise Performance

The present invention provides a cosmetic composition for enhancing exercise performance, which contains a chrysanthemum extract as an active ingredient.

In addition, the present invention provides a cosmetic composition for enhancing exercise performance, which contains 3,5-dicaffeoylquinic acid of Formula 1 or a pharmaceutically acceptable salt thereof as an active ingredient.

The chrysanthemum may be a plant of the genus *Chrysanthemum* in the family Asteraceae, and is called *Chrysanthemum morifolium*, and the chrysanthemum has been described above.

As the 3,5-dicaffeoylquinic acid of Formula 1, a compound isolated or synthesized from the chrysanthemum extract or a commercially available compound may be used, and details are the same as described above.

Hereinafter, to help in understanding the present invention, exemplary examples will be suggested. However, the following examples are merely provided to more easily understand the present invention, and not to limit the present invention.

EXAMPLES

Example 1. Preparation of Chrysanthemum Extract (1) Preparation of Methanol Extract of Chrysanthemum Dry chrysanthemum was ground with a mixer, 10 g of the ground chrysanthemum sample was added to 100 mL of methanol, and was extracted while stirring at 28° C. for 180 minutes. The extracted sample was filtrated under reduced pressure using a Whatman No. 2 filter, and the resulting filtrate was concentrated using a vacuum rotary concentrator to remove a solvent component, thereby preparing a methanol extract of chrysanthemum.

(2) Preparation of Ethanol Extract of Chrysanthemum

A process was performed by the same method as described in Example 1-(1), except that 10%, 30%, 50%, 70%, 90% or 95% ethanol was used, and as a result, a 10%, 30%, 50%, 70%, 90% or 95% ethanol extract of chrysanthemum was prepared.

(3) Preparation of Ethyl Acetate Extract of Chrysanthemum

A process was performed by the same method as described in Example 1-(1), except that ethyl acetate was used, and as a result, an ethyl acetate extract of chrysanthemum was prepared.

(4) Preparation of Hexane Extract of Chrysanthemum

A process was performed by the same method as described in Example 1-(1), except that hexane was used, and as a result, a hexane extract of chrysanthemum was prepared.

(5) Preparation of Hot Water Extract of Chrysanthemum

Dry chrysanthemum was ground with a mixer, 10 g of the ground chrysanthemum sample was added to 100 mL of water, and was extracted while stirring at 82° C. for 180 minutes. Afterward, a process was performed by the same method as described in Example 1-(1), and as a result, a hot water extract of chrysanthemum was prepared.

(6) Preparation of Chloroform Extract of Chrysanthemum

A process was performed by the same method as described in Example 1-(5), except that chloroform was used, and as a result, a chloroform extract of chrysanthemum was prepared.

(7) Preparation of Ultrahigh Pressure Extract of Chrysanthemum

Dry chrysanthemum was ground with a mixer, and 1 g of the ground chrysanthemum sample and 76 mL of 18% ethanol were put into a polyethylene pack, and extracted using an ultra-high pressure extractor (Frescal MFP-7000; Mitsubishi Heavy Industries, Tokyo, Japan). Conditions for ultra-high pressure extraction included an extraction pressure of 320 MPa and an extraction time of 5 minutes. The extracted sample was filtered with a Whatman No. 2 filter, the resulting filtrate was concentrated using a vacuum rotary concentrator to remove a solvent component, thereby preparing an ultra-high pressure extract of chrysanthemum.

(8) Preparation of Supercritical Extract of Chrysanthemum

Dry chrysanthemum was ground with a mixer, 1 g of the ground chrysanthemum sample was charged into a sample cartridge, and extracted using a supercritical fluid extractor (SFX 3560, Isco Inc., Lincoln, Nebr., USA). Conditions for supercritical fluid extraction included an extraction pressure of 20 MPa, an extraction temperature of 60° C., a supercritical $CO_2$ flow rate of 60 mL/min, and an extraction time of 60 minutes. When the supercritical fluid extraction was completed, a pressure of the extractor was reduced to terminate a supercritical fluid state, thereby obtaining a chrysanthemum supercritical fluid extract.

(9) Preparation of Subcritical Extract of Chrysanthemum

Dry chrysanthemum was ground with a mixer, 50 g of the ground chrysanthemum and 1 L of water were put into a subcritical water reactor in a subcritical extractor (Biovan, Gyeonggi, Korea) and then sealed. After sealing, a temperature of the reactor was increased up to 200° C., and when the temperature of the reactor reached 200° C., the temperature was maintained for 20 minutes for extraction. After 20 minutes, the extract was transferred to a storage tank to which cold water was provided to be rapidly cooled down to 30° C., and to isolate a suspended residue, only a supernatant was subjected to centrifugation at 3,600 rpm for 30 minutes. A solvent was thoroughly removed using a freeze dryer (IlShin Lab Co. Ltd., Seoul, Korea), thereby obtaining a subcritical extract of chrysanthemum.

Example 2. Isolation of 3,5-dicaffeoylquinic Acid

The ethanol extract of chrysanthemum prepared in Example 1-(2) was dissolved in 2 L of water, and isolated in three different solvents using ethyl acetate and n-butanol. The n-butanol solvent portion was loaded in an RP-18-filled column, and fractionated with a solvent system which changes a methanol ratio from 15 to 70%. According to the fractionation sequence, 16 subfractions were obtained. The seventh fraction was concentrated again using a vacuum rotary concentrator to remove a solvent component. The concentrate was loaded in a RP-18-filled column, and then fractioned with methanol. According to the fractionation sequence, 6 subfractions were obtained. Among these, 3,5-dicaffeoylquinic acid, which is the compound of the following Formula 1, was isolated and purified from the second fraction.

[Formula 1]

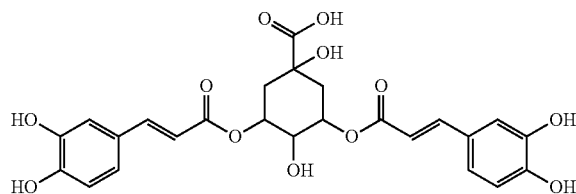

Example 3. Analysis of Content of 3,5-Dicaffeoylquinic Acid Contained in Ethanol Extract of Chrysanthemum Dry chrysanthemum was ground with a mixer, 10 g of the ground chrysanthemum sample was added to 100 mL of 30% ethanol and extracted at 70° C. for 3 hours. The extracted sample was filtrated under low pressure with a Whatman No. 2 filter, the filtered extract solution was concentrated with a vacuum rotary concentrator to remove a solvent component, thereby preparing a 30% ethanol extract of chrysanthemum, and here, a yield of the chrysanthemum extract was 23.24%. A content of 3,5-dicaffeoylquinic acid, which is the compound of the following Formula 1, in the chrysanthemum extract was analyzed by high-performance liquid chromatography (HPLC, YL9100 HPLC system; Younglin Instruments CO., Ltd., Gyeonggi, Korea). For HPLC analysis, 0.01% phosphoric acid and an acetonitrile solvent were used, and a 30% ethanol extract of chrysanthemum was analyzed at a wavelength of 330 nm and a flow rate of 1.0 mL/min. The 3.5-dicaffeoylquinic acid was detected at a retention time of 11 minutes, and contained at 2.17% in the 30% ethanol extract of chrysanthemum.

EXPERIMENTAL EXAMPLES

Experimental Example 1. Analysis of Exercise Performance Effect of Chrysanthemum Extract (1) Activity of Increasing PPARδ by Treatment with Chrysanthemum Extract An experiment was performed by a known method using a vector having a luciferase gene under the control of a plasmid expressing PPARδ and PPRE (Cell, 68: 879-887, 1992; J. Biol. Chem., 272: 25252-25259, 1997).

COS7 cells (CV-1 in Origin Simian-7, ATCC, Manassas, Va., USA) which do not express a PPAR-related gene were cultured in Dulbecco Modified Eagle Medium (DMEM, Hyclone, Logan, Utah, USA) containing 10% fetal bovine serum (FBS, Gibco, Gaithersburg, Md., USA), and then cultured in a 24-well plate for 5 hours or longer. For transfection, a plus reagent (Aptabio, Gyeonggi, Korea), a PPARδ plasmid and a pFR-luciferase vector (Stratagene, La Jolla, Calif., USA) were mixed together with serum-free DMEM (Hyclone), incubated for 15 minutes, mixed with a Lipofecter reagent (Aptabio), incubated again at room temperature for 15 minutes, and then dropped on the cells. After 4 hours, the medium was replaced with a 10% FBS (Gibco)-containing DMEM (Hyclone), and stabilized for 24 hours. The 10%, 30%, 50%, 70% or 90% ethanol extract of chrysanthemum, which were prepared in Example 1-(2), or the hot water extract of chrysanthemum, which was prepared in Example 1-(5), were treated at 10 μg/mL, and a degree of activating a ligand binding domain was quantified by adding a luciferase substrate (Promega, Madison, Wis., USA) and using a Microlumateplus LB 96V luminometer (Berthlod, Wildbab, Germany). The result is shown in FIG. 1.

As a result, as shown in FIG. 1, the hot water extract of chrysanthemum, and the 10%, 30%, 50% and 70% ethanol extracts significantly increased PPARδ activity (*p<0.05). This means that the chrysanthemum extract of the present invention is a ligand of PPARδ and has an excellent ability to activate PPARδ.

(2) Activity of Increasing PGC-1α by Treatment with Chrysanthemum Extract

To confirm an effect of increasing an expression level of PGC-1α by treatment of COS7 cells with a chrysanthemum extract, COS7 cells (ATCC) were transfected with a pTA-Luc-PGC-1α plasmid (Addgene) by the same method as described in Experimental Example 1-(1). Here, 10%, 30%, 50%, 70% and 90% ethanol extracts of chrysanthemum, which were prepared in Example 1-(2), and the hot water extract of chrysanthemum, which was prepared in Example 1-(5), were treated at 10 ng/mL. The result is shown in FIG. 2.

Figure 2:
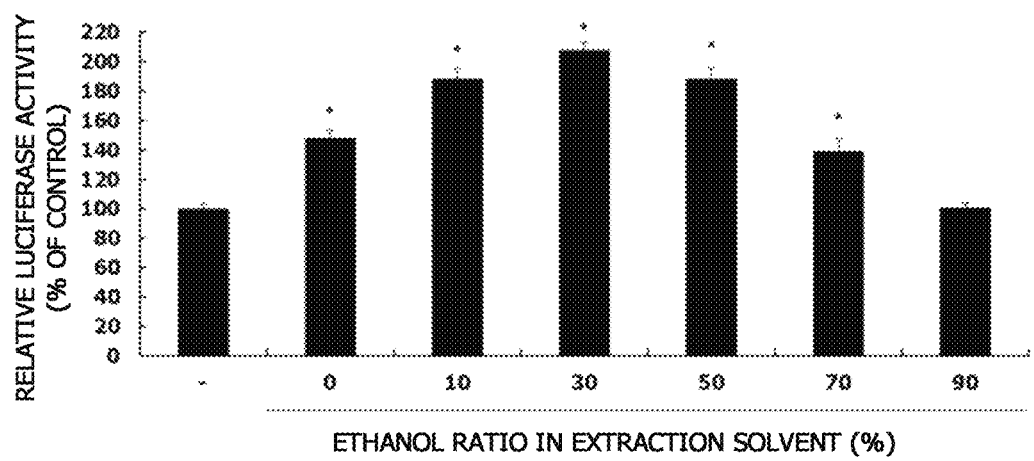
FIG. 2 shows a result of measuring expression levels of PGC-1α according to treatment with a chrysanthemum optimized hot water extract and 10%, 30%, 50%, 70% and 90% ethanol extracts.

As a result, as shown in FIG. 2, the hot water extract of chrysanthemum and 10%, 30%, 50% and 70% ethanol extracts significantly increased the activity of PGC-1α, which is a main factor involved in mitochondrial biogenesis (*p<0.05). This means that an ability of the chrysanthemum extract of the present invention to promote mitochondrial biogenesis by activating PGC-1α is excellent.

(3) PPARδ Increasing-Activity of 95% Ethanol Extract of Chrysanthemum

Figure 3:
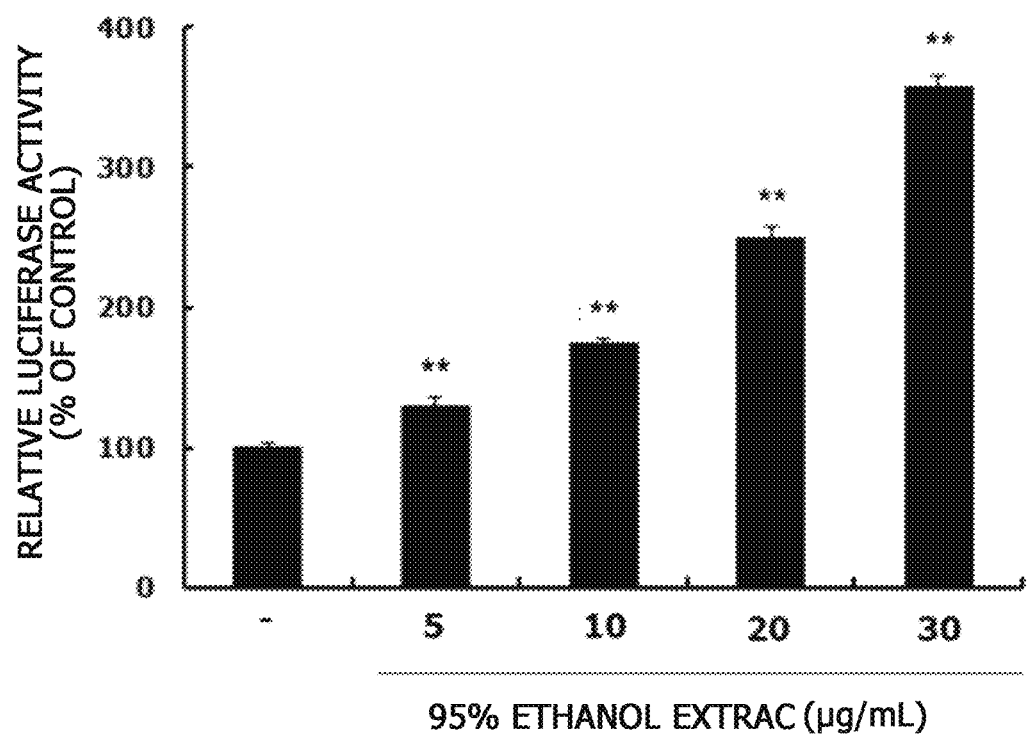
FIG. 3 shows a result of measuring the activity of a PPARδ ligand binding domain according to treatment with a 95% ethanol extract of chrysanthemum.

To confirm an effect of increasing PPARδ activity by treatment with a 95% ethanol extract of chrysanthemum in COS7 cells (ATCC), a degree of activating a ligand binding domain when the 95% ethanol extract of chrysanthemum, prepared in Example 1-(2), was treated at 5, 10, 20 or 30 μg/mL by the same method as described in Experimental Example 1-(1) is shown in FIG. 3.

As a result, as shown in FIG. 3, the 95% ethanol extract of chrysanthemum increased PPARδ activity in a concentration-dependent manner, and compared with a control group, exhibited a significant difference (**p<0.01). This means that the 95% ethanol extract of chrysanthemum according to the present invention is a ligand of PPARδ and has an excellent ability to activate PPARδ.

(4) SIRT1 Increasing-Activity of 95% Ethanol Extract of Chrysanthemum

To confirm an effect of increasing an expression level of SIRT1 by treatment of COS7 cells (ATCC) with a chrysanthemum extract, COS7 cells (ATCC) were transfected with a pTA-Luc-SIRT1 plasmid (Addgene) by the same method as described in Experimental Example 1-(1). Here, the 95% ethanol extract of chrysanthemum prepared in Example 1-(2) was treated at 20, 30 or 40 μg/mL, and the result is shown in FIG. 4.

Figure 4:
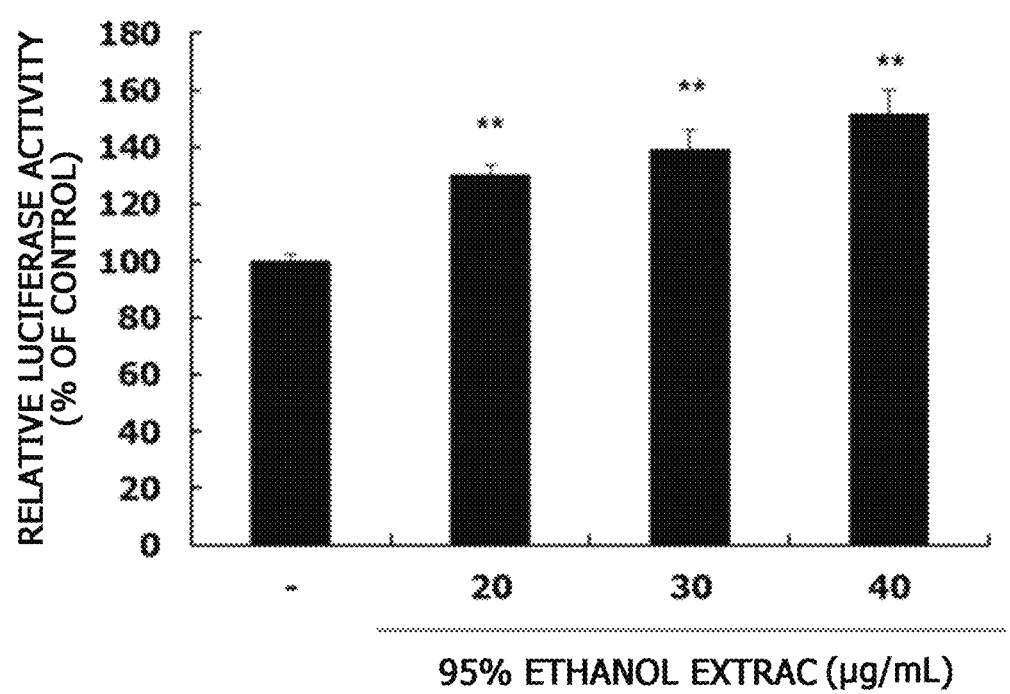
FIG. 4 shows a result of measuring an expression level of SIRT1 according to treatment with a 95% ethanol extract of chrysanthemum.

As a result, as shown in FIG. 4, the 95% ethanol extract of chrysanthemum significantly increased an expression level of SIRT1, which is a main factor involved in mitochondrial biogenesis (**p<0.01). This means that the 95% ethanol extract of chrysanthemum according to the present invention increases mitochondrial biogenesis, and has an excellent ability to increase exercise performance.

(5) PGC-1α Increasing-Activity of 95% Ethanol Extract of Chrysanthemum

To confirm an effect of increasing an expression level of PGC-1α by treatment of COST cells (ATCC) with the 95% ethanol extract of chrysanthemum, the 95% ethanol extract of chrysanthemum, prepared in Example 1-(2), was treated at 10 or 40 μg/mL by the same method as described in Experimental Example 1-(2). The result is shown in FIG. 5.

Figure 5:
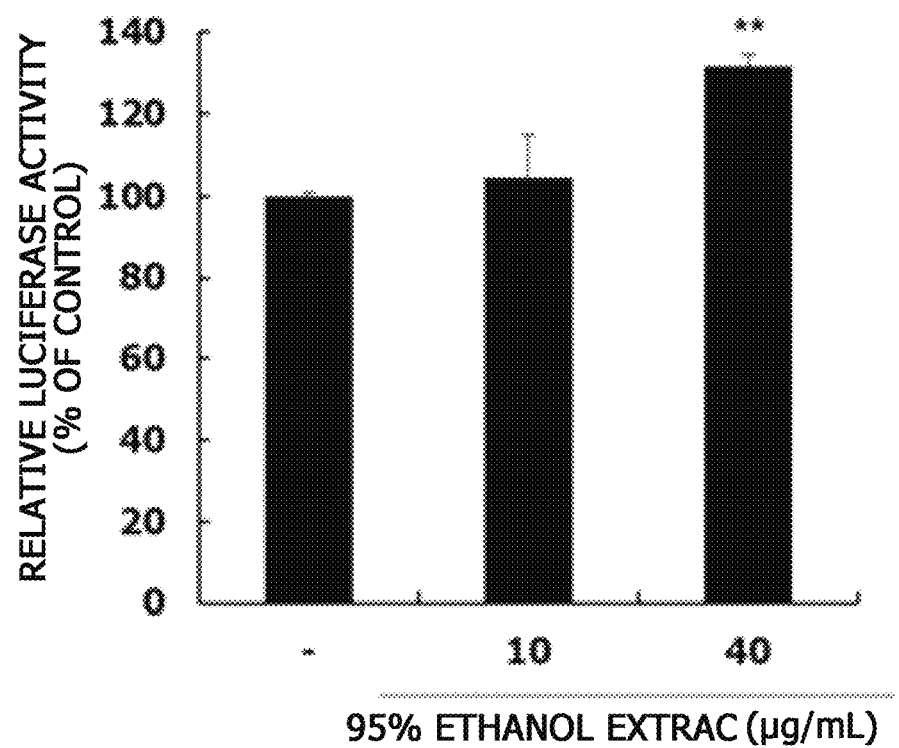
FIG. 5 shows a result of measuring an expression level of PGC-1α according to treatment with a 95% ethanol extract of chrysanthemum.

As a result, as shown in FIG. 5, 40 μg/mL of the 95% ethanol extract of chrysanthemum significantly increased PGC-1α activity, which is a main factor involved in mitochondrial biogenesis (**p<0.01). This means that the 95% ethanol extract of chrysanthemum according to the present invention activates PGC-1α and thus has an excellent ability to promote mitochondrial biogenesis.

(6) Mitochondrial Biogenesis-Promoting Activity of 30% Ethanol Extract of Chrysanthemum L6 myoblasts (ATCC), which are muscle cells, were added at $1 \times 10^5$ cell/mL to a 6-well plate with 10% FBS (Gibco)-containing DMEM (Hyclone). When the cell density reached approximately 80 to 85%, the medium in the well was removed, and then the cells were treated with the 30% ethanol extract of chrysanthemum prepared in Example 1-(2), which was dissolved in 2% HS (Hyclone)-containing DMEM (Hyclone) at 5, 10 or 20 μg/mL, to induce myotube differentiation. Here, the differentiation was performed for total of 6 days by replacing the medium and a sample with fresh ones every two days. After the differentiation induction, the medium was suctioned, and 100 nM Mitotracker (Thermo Fisher Scientific Inc., Waltham, Mass., USA) dissolved in DMEM (Hyclone) was treated for 30 minutes. The medium was removed, 1 mL of a methanol solvent was added to each well, and fluorescence was measured at an absorption wavelength of 490 nm and an emission wavelength of 516 nm using a microplate reader (Versa Max, Sunnyvale, Calif., USA). The result is shown in FIG. 6.

Figure 6:
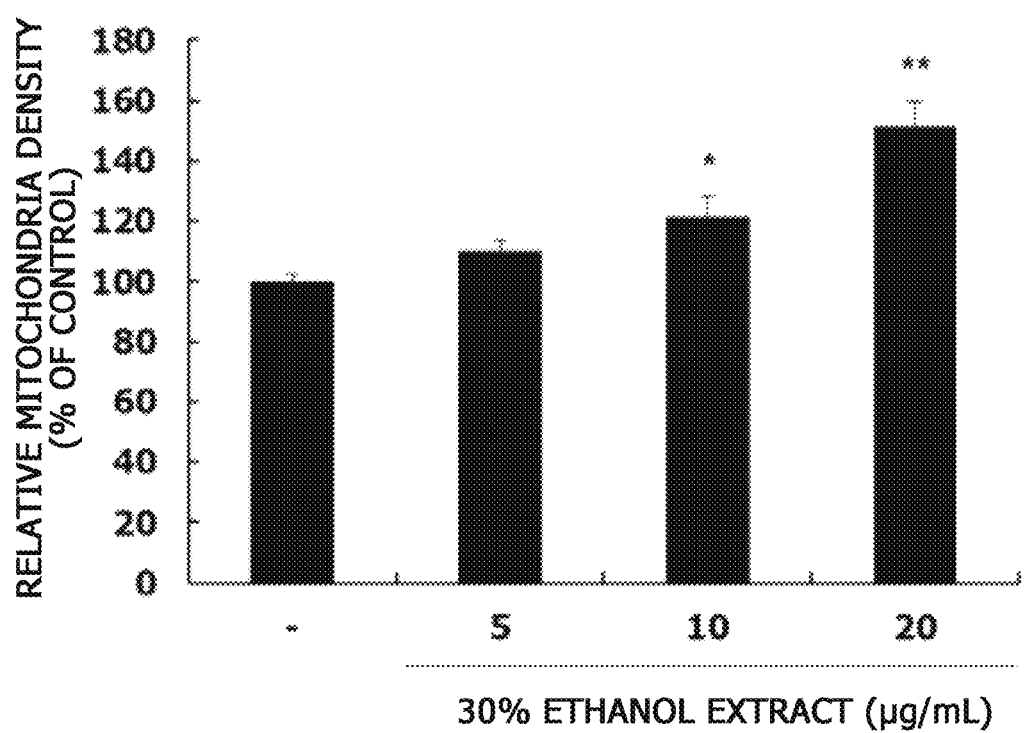
FIG. 6 shows a result of measuring an amount of mitochondrial biogenesis according to treatment with a 30% ethanol extract of chrysanthemum.

As a result, as shown in FIG. 6, the 30% ethanol extract of chrysanthemum significantly increased an amount of mitochondria in a muscle (*p<0.05, **p<0.01). This means that the 30% ethanol extract of chrysanthemum according to the present invention promotes mitochondrial biogenesis and has an excellent ability to increase exercise performance.

Figure 7:
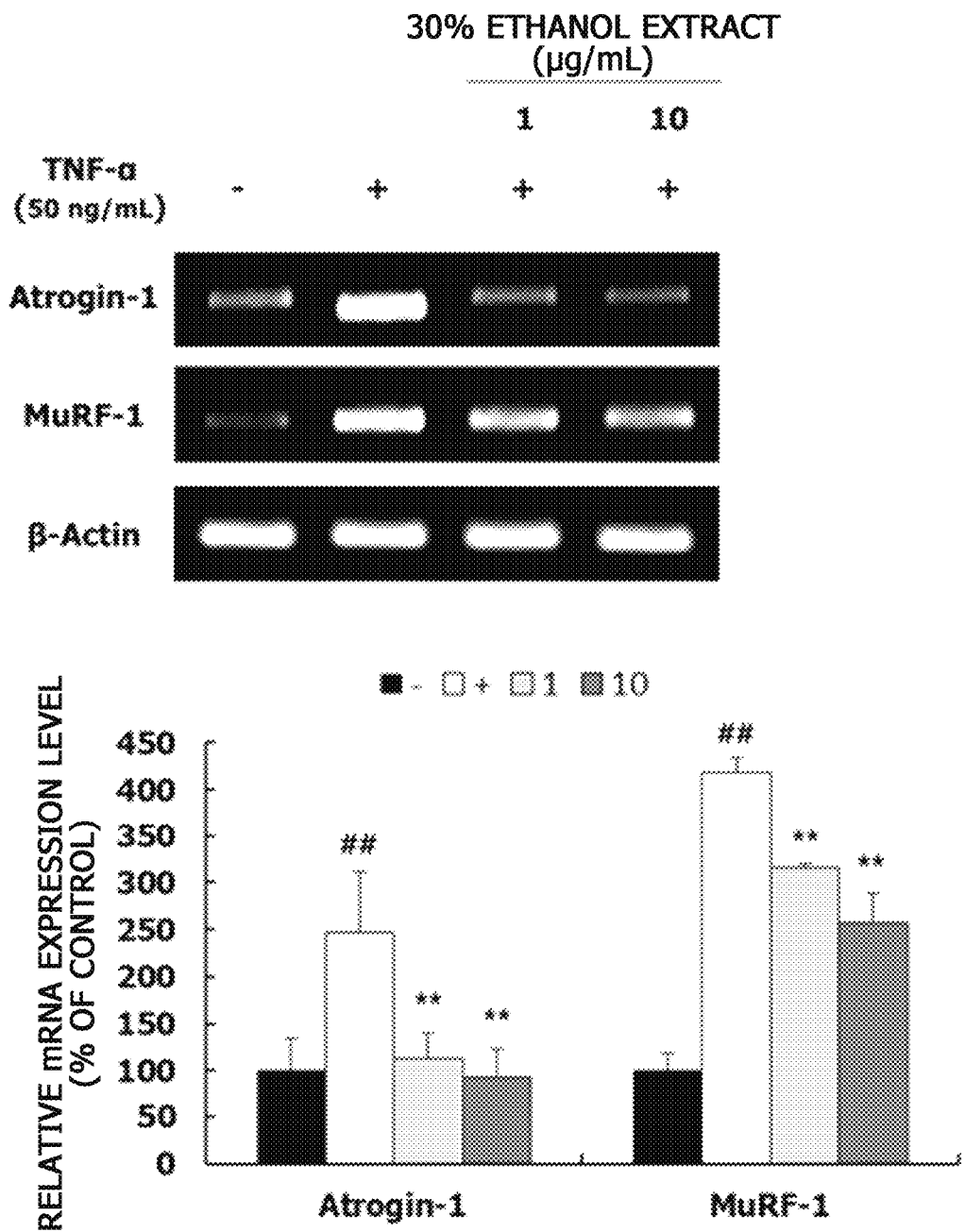
FIG. 7 shows a result of measuring mRNA expression levels of atrogin-1 and MuRF-1 according to treatment with a 30% ethanol extract of chrysanthemum.
Figure 8:
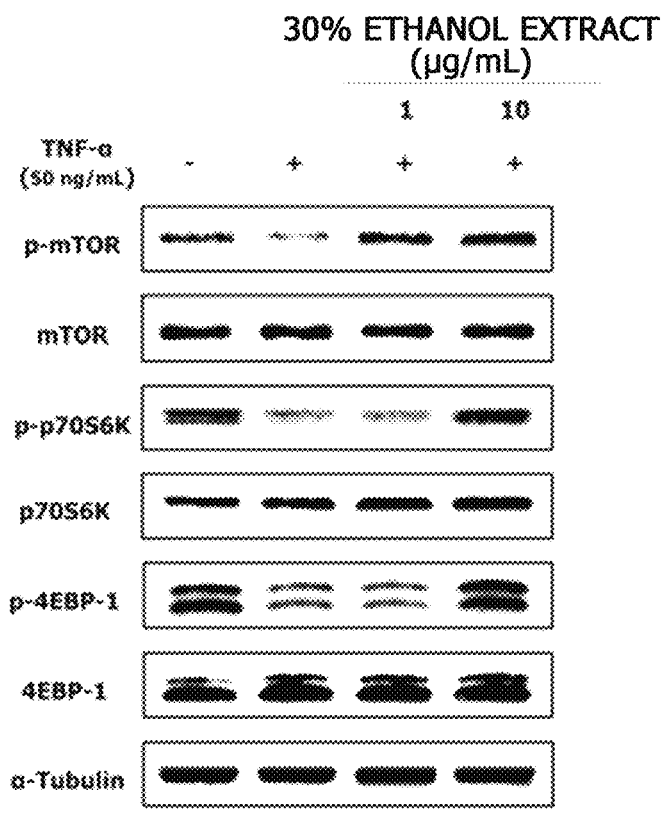
FIG. 8 shows a result of measuring protein expression levels of mTOR, p70S6K and 4EBP1 according to treatment with a 30% ethanol extract of chrysanthemum.
Figure 8:
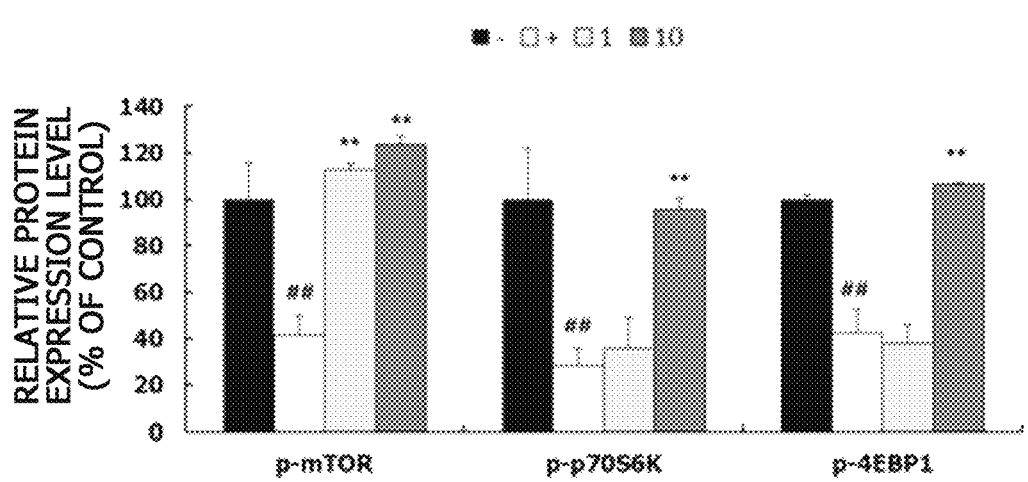

Experimental Example 2. Muscle Protein Degradation-Inhibiting Activity of 30% Ethanol Extract of Chrysanthemum L6 myoblasts (ATCC), which are muscle cells, were added at $1 \times 10^5$ cell/mL to a 6-well plate with 10% FBS (Gibco)-containing DMEM (Hyclone). When the cell density reached approximately 80 to 85%, the medium in the well was removed, the cells were treated with 2% HS (Hyclone)-containing DMEM (Hyclone) to induce myotube differentiation. The differentiation was performed for total of 6 days by replacing the medium and a sample with fresh ones every two days. After differentiation, the 30% ethanol extract of chrysanthemum prepared in Example 1-(2) was dissolved in DMEM (Hyclone) containing 50 ng/mL tumor necrosis factor alpha (TNF-α; PeproTech, Rocky Hills, N.J., USA) at 1 or 10 μg/mL, and used to treat the cells. After 6 hours, total RNA was isolated with a TRIzol reagent (Takara, Shiga, Japan). The isolated total RNA was quantified using a NanoDrop 1000 (Thermo Fisher Scientific Inc.). cDNA was synthesized from 16 μL of the quantified RNA using a Reverse Transcriptase Premix (ELPIS-Biotech, Daejeon, Korea) and a PCR machine (Gene Amp PCR System 2700; Applied Biosystems, Foster City, Calif., USA) under conditions of 42° C. for 55 minutes and 70° C. for 15 minutes. PCR was performed in 30 cycles using 4 μL out of 16 μL of the produced cDNA, specific primers (Bioneer, Daejeon, Korea) below and a PCR premix (ELPIS-Biotech) at 95° C. for 30 seconds, 60° C. for 1 minutes, and 72° C. for 1 minute. The sequences of the primers used in the PCR are shown in Table 1 below. The cDNA amplified by PCR was isolated by electrophoresis using a 1.5% agarose gel, and cDNA bands were identified using a G;BOX EF imaging system (Syngene, Cambridge, UK). The result is shown in FIG. 7.

containing a proteinase inhibitor cocktail (Sigma, St. Louis, Mo., USA). The cells dissolved in the buffer solution were transferred to a 1.5 mL tube for centrifugation at 13,000 rpm for 10 minutes, and then only a supernatant was taken. The supernatant obtained previously was quantified by a Bradford method (Bio-Rad Laboratories Inc., Hercules, Calif., USA). The quantified protein was boiled for 5 minutes and isolated by electrophoresis with a 10% SDS-PAGE gel, and then the isolated proteins were transferred to a nitrocellulose membrane. p-mTOR, mTOR, p-4EBP1, 4EBP1, p-P70S6K and P70S6K and an α-tubulin primary antibody were diluted in 2.5% bovine serum albumin (BSA; bioWORLD, Dublin, Ohio, USA) at a ratio of 1:1000, and the proteins which were transferred to a nitrocellulose membrane were reacted at room temperature for 20 hours. After the reaction with the primary antibody, the nitrocellulose membrane was washed with Tris-buffer Saline Tween 20 (TBST) three times for 10 minutes. After washing, a secondary antibody recognizing the primary antibody was diluted in 2.5% BSA at a ratio of 1:5000, and reacted with the nitrocellulose membrane at room temperature for 2 hours, and then the nitrocellulose membrane was washed with TBST three times each for 10 minutes. Protein bands were detected with western blotting detection reagents (Amersham, Tokyo, Japan), and visualized using a G;BOX EF imaging system (Syngene). The result is shown in FIG. 8.

TABLE 1

| Name of target gene | Primer sequence | Primer direction | Sequence No. |
|---|---|---|---|
| Atrogin-1 | 5'-CCCTGAGTGGCATCGCCCAA-3' | Forward | SEQ ID NO: 1 |
|  | 5'-AGGTCCCGCCCATCGCTCA-3' | Reverse | SEQ ID NO: 2 |
| MuRF-1 | 5'-TCTACTCGGCCACAGGCGCT-3' | Forward | SEQ ID NO: 3 |
|  | 5'-CTTGACAGCTCCCGCCGCAA-3' | Reverse | SEQ ID NO: 4 |
| β-Actin | 5'-AGCCATGTACGTAGCCATCC-3' | Forward | SEQ ID NO: 5 |
|  | 5'-CTCTCAGCTGTGGTGCTGAA-3' | Reverse | SEQ ID NO: 6 |

Consequently, as shown in FIG. 7, expression levels of the major biomarkers related to muscle protein degradation, such as atrogin-1 and MuRF-1, significantly increased ($p<0.01$) due to TNF-α, and the mRNA expression levels of atrogin-1 and MuRF-1, increased by TNF-α, were significantly decreased ($p<0.01$) by treating the 30% ethanol extract of chrysanthemum. This means that the 30% ethanol extract of chrysanthemum according to the present invention has an excellent ability to inhibit muscle protein degradation in muscle cells.

Experimental Example 3. Muscle Protein Synthesis-Promoting Activity of 30% Ethanol Extract of Chrysanthemum To confirm the muscle protein expression-increasing activity of a chrysanthemum extract in L6 myoblasts (ATCC), which are muscle cells, after differentiation by the same method as described in Experimental Example 2, a sample was treated with the 30% ethanol extract of chrysanthemum prepared in Example 1-(2) at 1 or 10 μg/mL. The samples were treated for 24 hours, and then the cells were dissolved in an NP-40 buffer solution (ELPIS-Biotech)

As shown in FIG. 8, protein expression levels of p-mTOR, p-4EBP1 and p-P70S6K, which are main biomarkers related to muscle protein production, were significantly decreased by TNF-α ($p<0.01$), and the p-mTOR, p-4EBP1 and p-P70S6K protein expression levels, which were reduced by TNF-α, were significantly increased by the treatment with the 30% ethanol extract of chrysanthemum ($p<0.01$). This means that the 30% ethanol extract of chrysanthemum of the present invention has an excellent ability to increase muscle production in muscle cells.

Experimental Example 4. Muscle Differentiation-Promoting Activity of 30% Ethanol Extract of Chrysanthemum To confirm the muscle differentiation-promoting activity of a chrysanthemum extract in L6 myoblasts (ATCC), which are muscle cells, the cells were treated with the 30% ethanol extract of chrysanthemum, prepared in Example 1-(2), at 5, 10 or 20 μg/mL to induced myotube differentiation by the same method as described in Experimental Example 1-(6). RT-PCR was performed with specific primers (Bioneer) by the same method as described in Experimental Example 2, and the result is shown in FIG. 9.

TABLE 2

| Name of target gene | Primer sequence | Primer direction | Sequence No. |
|---|---|---|---|
| MyoD | 5'-GGATGGTGCCCCTGGGTCCT-3' | Forward | SEQ ID NO: 7 |
| | 5'-TGGCCTTCGCTGTGAGTCGC-3' | Reverse | SEQ ID NO: 8 |
| Myogenin | 5'-TGGGCTGCCACAAGCCAGAC-3' | Forward | SEQ ID NO: 9 |
| | 5'-CAGCCCAGCCACTGGCATCA-3' | Reverse | SEQ ID NO: 10 |
| β-Actin | 5'-CTGTGTGGATTGGTGGCTCTAT-3' | Forward | SEQ ID NO: 11 |
| | 5'-GTGTAAAACGCAGCTCAGTAACA-3' | Reverse | SEQ ID NO: 12 |

Figure 9:
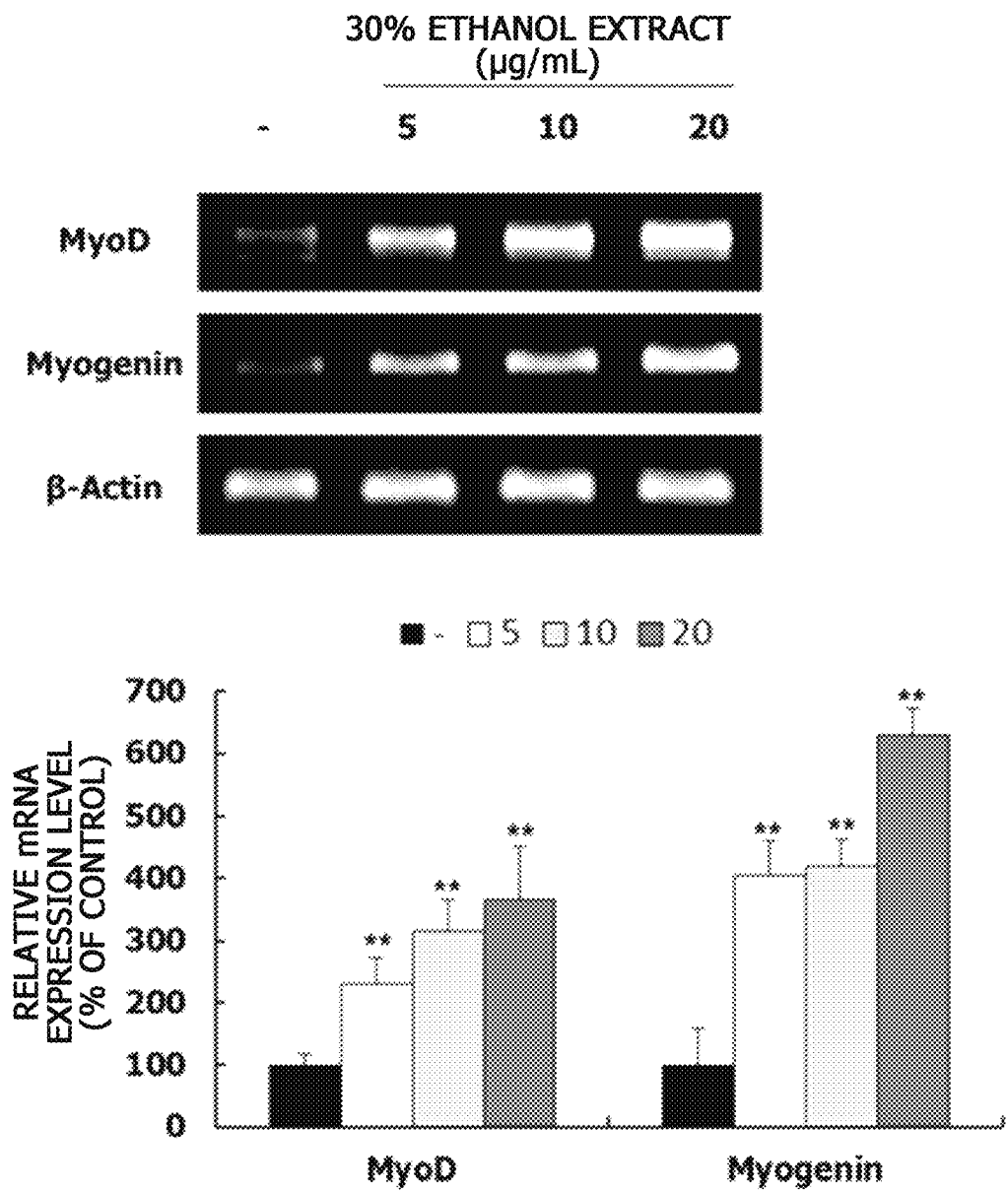
FIG. 9 shows a result of measuring mRNA expression levels of MyoD and myogenin according to treatment with a 30% ethanol extract of chrysanthemum.

As shown in FIG. 9, when the 30% ethanol extract of chrysanthemum was treated, mRNA expression of MyoD and myogenin, which are main genes related to differentiation activity of muscle cells, was significantly increased (**p<0.01). This means that the 30% ethanol extract of chrysanthemum of the present invention has an excellent effect of promoting muscle differentiation in muscle cells.

Experimental Example 5. Exercise Performance of 3,5-dicaffeoylquinic Acid (1) SIRT1 Increasing Activity To confirm an effect of increasing an expression level of SIRT1 by treatment of COS7 cells (ATCC) with 3,5-dicaffeoylquinic acid, the 3,5-dicaffeoylquinic acid obtained in Example 2 was treated at 5, 10, 20, 40 or 60 μg/mL by the same method as described in Experimental Example 1-(4), and the result is shown in FIG. 10.

Figure 10:
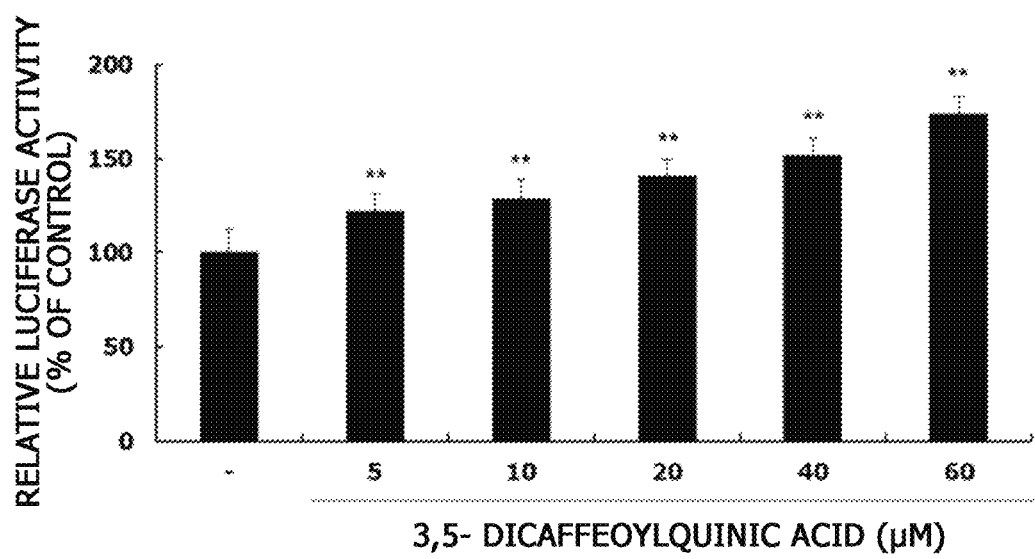
FIG. 10 shows a result of measuring an expression level of SIRT1 according to treatment with 3,5-dicaffeoylquinic acid.

As a result, as shown in FIG. 10, when 3,5-dicaffeoylquinic acid was treated at 20, 40 or 60 μg/mL, the expression level of SIRT1 was significantly increased (**p<0.01). This means that the 3,5-dicaffeoylquinic acid of the present invention activates SIRT1 and thus has an excellent ability to promote mitochondrial biogenesis.

(2) PGC-1α Increasing Activity

Figure 11:
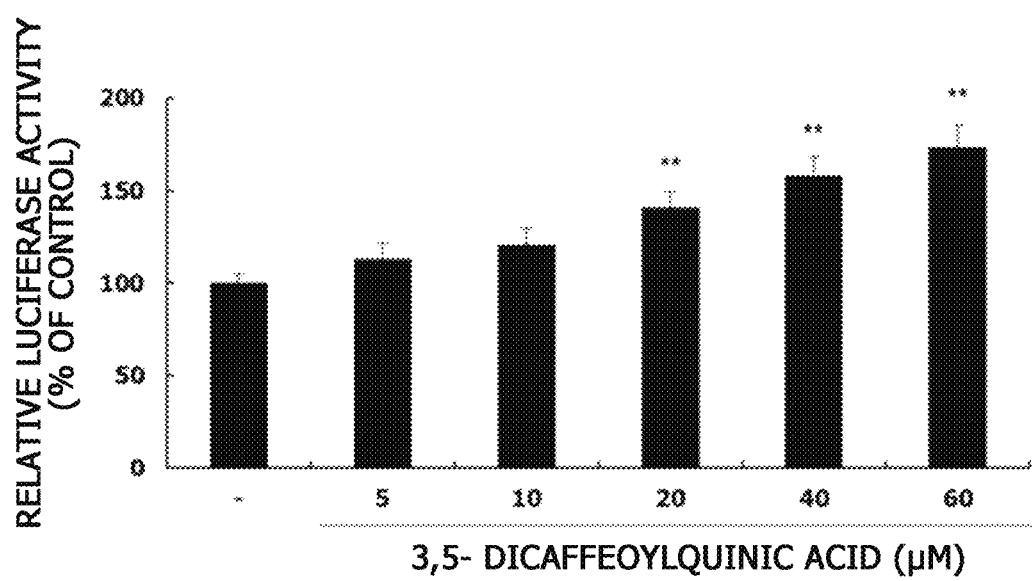
FIG. 11 shows a result of measuring an expression level of PGC-1α according to treatment with 3,5-dicaffeoylquinic acid.

To confirm an effect of increasing an expression level of PGC-1α by treatment of COS7 cells (ATCC) with 3,5-dicaffeoylquinic acid, the 3,5-dicaffeoylquinic acid obtained in Example 2 was treated at 5, 10, 20, 40 or 60 μg/mL by the same method as described in Experimental Example 1-(2), and the result is shown in FIG. 11.

As a result, as shown in FIG. 11, when 3,5-dicaffeoylquinic acid was treated at 5, 10, 20, 40 or 60 μg/mL, an expression level of PGC-1α, which is a main factor involved in mitochondrial biogenesis was significantly increased (**p<0.01). This means that the 3,5-dicaffeoylquinic acid of the present invention activates PGC-1α and thus has excellent ability to promote mitochondrial biogenesis.

Experimental Example 6. Muscle Protein Degradation-Inhibiting Activity of 3,5-Dicaffeoylquinic Acid To confirm muscle protein degradation-inhibiting activity by treatment of L6 myoblasts (ATCC), which are muscle cells, with 3,5-dicaffeoylquinic acid, the cells were treated with the 3,5-dicaffeoylquinic acid obtained in Example 2 at 1 or 10 lit/mL, and then mRNA expression levels of atrogin-1 and MuRF-1 were confirmed by the same method as described in Experimental Example 2. The result is shown in FIG. 12.

Figure 12:
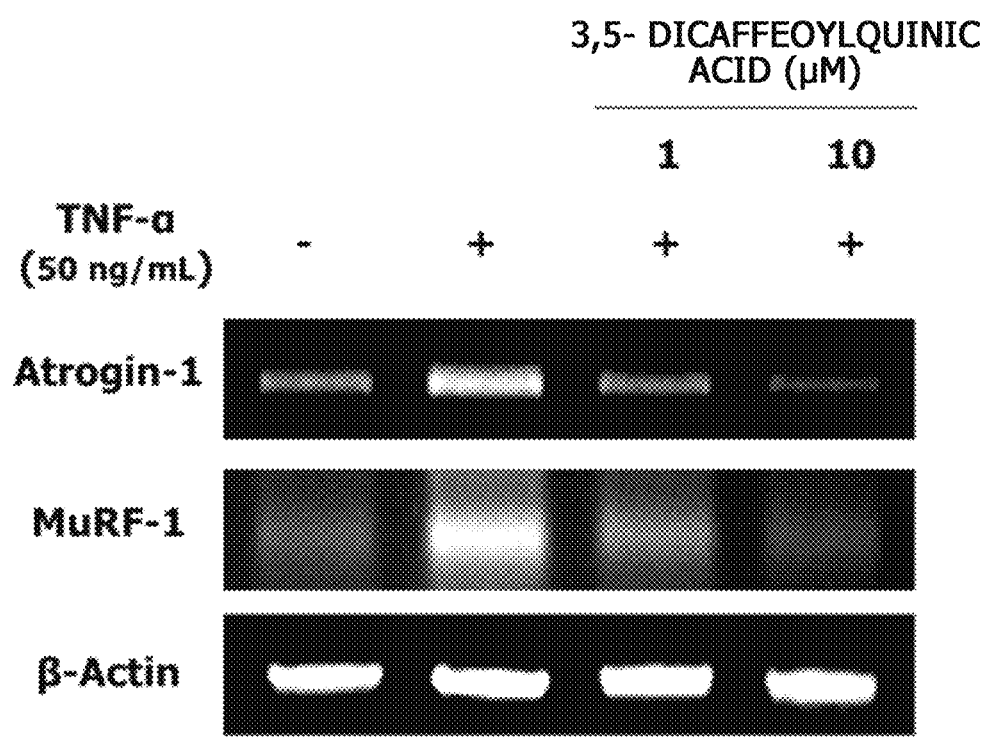
FIG. 12 shows a result of measuring mRNA expression levels of atrogin-1 and MuRF-1 according to treatment with 3,5-dicaffeoylquinic acid.

As a result, as shown in FIG. 12, expression levels of atrogin-1 and MuRF-1, which are the main biomarkers involved in muscle protein degradation, were increased by TNF-α, and mRNA expression of atrogin-1 and MuRF-1, which were increased by TNF-α, was decreased in a concentration dependent manner by treatment with 3,5-dicaffeoylquinic acid. This means that the 3,5-dicaffeoylquinic acid of the present invention has an excellent ability to inhibit muscle protein degradation in muscle cells.

Experimental Example 7. Muscle Protein Synthesis-Promoting Activity of 3,5-dicaffeoylquinic Acid To confirm muscle protein synthesis-promoting activity by treatment of L6 myoblasts (ATCC), which are muscle cells, with 3,5-dicaffeoylquinic acid, the cells were treated with the 3,5-dicaffeoylquinic acid obtained in Example 2 at 1 or 10 μg/mL and an expression level of the p-mTOR protein was confirmed by the same method as described in Experimental Example 3. The result is shown in FIG. 13.

Figure 13:
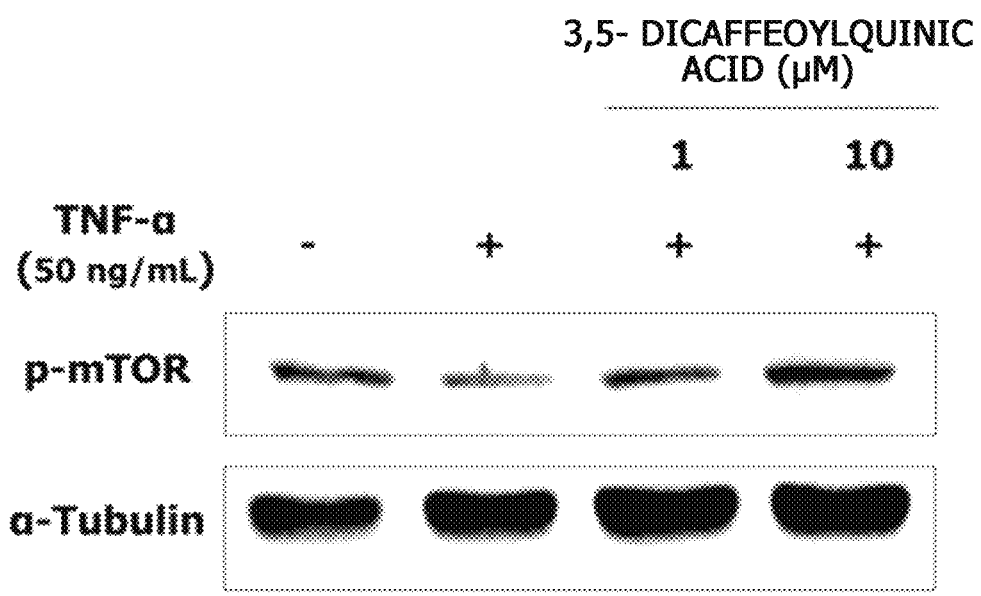
FIG. 13 shows a result of measuring an mTOR protein expression level according to treatment with 3,5-dicaffeoylquinic acid.

As a result, as shown in FIG. 13, expression levels of p-mTOR, p-4EBP1 and p-P70S6K proteins, which are the main biomarkers involved in muscle protein production, were decreased by TNF-α, and an expression level of the p-mTOR protein, which was decreased by treatment with 3,5-dicaffeoylquinic acid, was increased in a concentration-dependent manner. This means that the 3,5-dicaffeoylquinic acid of the present invention has an excellent ability to increase muscle production in muscle cells.

Experimental Example 8. Muscle Differentiation-Promoting Activity of 3,5-Dicaffeoylquinic Acid To confirm muscle protein synthesis-promoting activity by treatment of L6 myoblasts (ATCC), which are muscle cells, with 3,5-dicaffeoylquinic acid, the cells were treated with the 3,5-dicaffeoylquinic acid obtained in Example 2 at 10, 20 or 40 μg/mL, and then mRNA expression levels of MyoD and myogenin were confirmed by the same method as described in Experimental Example 4. The result is shown in FIG. 14.

Figure 14:
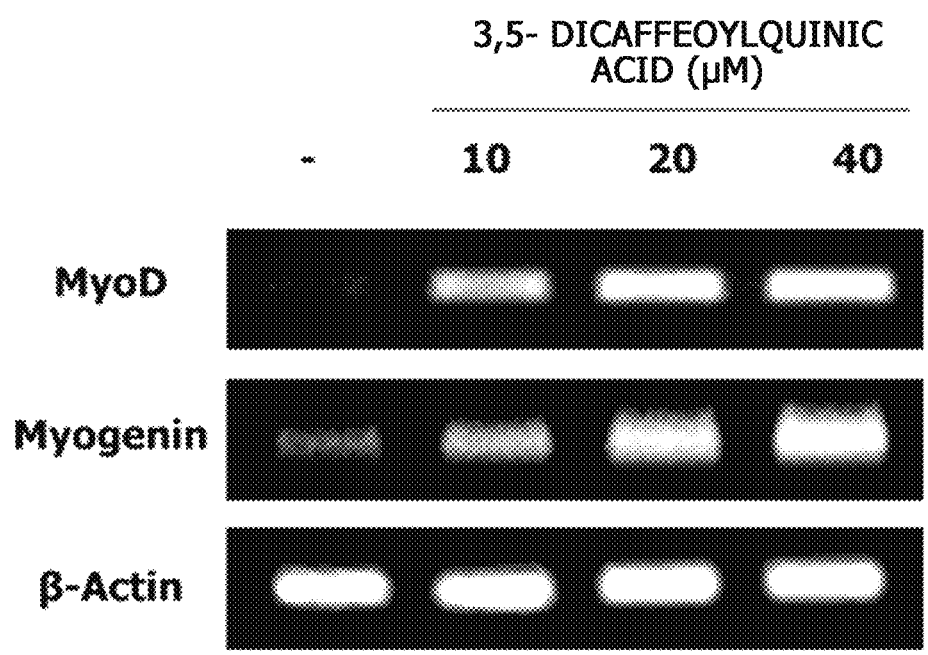
FIG. 14 shows a result of measuring mRNA expression levels of MyoD and myogenin according to treatment with 3,5-dicaffeoylquinic acid.

As a result, as shown in FIG. 14, mRNA expression levels of MyoD and myogenin, which are main factors involved in muscle differentiation in the L6 muscle cells, were increased in a concentration-dependent manner by treatment with 3,5-dicaffeoylquinic acid. This means that the 3,5-dicaffeoylquinic acid of the present invention has an excellent ability to promote muscle differentiation in muscle cells.

Hereinafter, preparation examples of compositions containing an extract and components of the present invention will be described below, but this is for specific description of the present invention without limitation thereto.

PREPARATION EXAMPLES

Preparation Example 1: Preparation of Powder 20 mg of chrysanthemum extract or 3,5-dicaffeoylquinic acid
100 mg of fructose hydrate
10 mg of talc
The components were mixed, and then an airtight pouch was charged with the mixture, thereby preparing a powder.

Preparation Example 2: Preparation of Tablet 10 mg of chrysanthemum extract or 3,5-dicaffeoylquinic acid
100 mg of corn starch
100 mg of fructose hydrate
2 mg of magnesium stearate The components were mixed, and then tableted by a conventional method of preparing a tablet, thereby preparing a tablet.

Preparation Example 3: Preparation of Capsule 10 mg of chrysanthemum extract or 3,5-dicaffeoylquinic acid
3 mg of microcrystalline cellulose
14.8 mg of fructose hydrate
0.2 mg of magnesium stearate The components were mixed, and then a gelatin capsule was filled with the mixture by a conventional method of preparing a capsule, thereby preparing a capsule.

Preparation Example 4: Preparation of Injection 10 mg of chrysanthemum extract or 3,5-dicaffeoylquinic acid
180 mg of mannitol
2974 mg of sterilized distilled water for injection
26 mg of sodium monohydrogen phosphate The components were mixed, and then an injection was prepared to include the mixture of the components at the above-mentioned contents per ampoule (2 mL) by a conventional method of preparing an injection.

Preparation Example 5: Preparation of Liquid 10 mg of chrysanthemum extract or 3,5-dicaffeoylquinic acid
10 mg of isomerized sugar
5 mg of mannitol
Distilled water q.s.
Lemon flavor q.s.

According to a conventional preparation method, each component was dissolved in distilled water, the lemon flavor was added in a sufficient amount, the distilled water was added to become a total volume to 100 mL, and the mixture was sterilized. A brown bottle was filled with the sterilized mixture, thereby preparing a liquid.

Preparation Example 6: Preparation of Health Functional Food 10 mg of chrysanthemum extract or 3,5-dicaffeoylquinic acid
Vitamin mixture q.s.
70 μg of vitamin A acetate
1.0 mg of vitamin E
0.13 mg of vitamin B1
0.15 mg of vitamin B2
0.5 mg of vitamin B6
0.2 μg of vitamin B12
10 mg of vitamin C
10 μg of biotin
1.7 mg of nicotinamide
50 μg of folic acid
0.5 mg of calcium pantothenate
Mineral mixture q.s.
1.75 mg of ferrous sulfate
0.82 mg of zinc oxide
25.3 mg of magnesium carbonate
15 mg of monopotassium phosphate
55 mg of dicalcium phosphate
30 mg of potassium citrate
100 mg of calcium carbonate
24.8 mg of magnesium chloride Although a mixture of the vitamins and minerals was prepared by mixing components relatively suitable for health food as a preferable example, a mixing ratio of these components may be arbitrarily changed. The above-mentioned components were mixed by a conventional method of preparing health food, thereby preparing granules, which may be used to prepare a composition for health food according to a conventional method.

Preparation Example 7: Preparation of Health Drink 10 mg of chrysanthemum extract or 3,5-dicaffeoylquinic acid
15 g of vitamin C
100 g of vitamin E (powder)
19.75 g of ferrous lactose
3.5 g of zinc oxide
3.5 g of nicotinamide
0.2 g of vitamin A
0.25 g of vitamin B1
0.3 g of vitamin B2
Distilled water q.s.

The above-mentioned components were mixed by a conventional method of preparing a food drink and heated while stirring at 85° C. for approximately 1 hour, and the prepared solution was filtered, contained in a sterilized 2 L container, sealed, stored in a refrigerator, and then used to prepare a composition for a health drink of the present invention.

Although components relatively suitable for a favorite drink were mixed as a preferable example, a mixing ratio may be arbitrarily changed according to regional and national preferences such as the demand level, the country of demand, a purpose of use, etc.

Preparation Example 8: Preparation of Nourishing Toner (Milk Lotion)

2.0 wt % of chrysanthemum extract or 3,5-dicaffeoylquinic acid
5.0 wt % of squalene
4.0 wt % of cera
1.5 wt % of polysorbate 60
1.5 wt % of sorbitan sesquioleate
0.5 wt % of liquid paraffin
5.0 wt % of caprylic/capric triglyceride
3.0 wt % of glycerin
3.0 wt % of butylene glycol
3.0 wt % of propylene glycol
0.1 wt % of carboxy vinyl polymer
0.2 wt % of triethanolamine
Preservative, colorant, flavor q.s.
100 wt % of distilled water Although components relatively suitable for a nourishing toner were mixed as a preferable example, a mixing ratio may be arbitrarily changed. The nourishing toner may be prepared by a conventional method used in the cosmetics field.

Preparation Example 9: Preparation of Skin Toner (Skin Lotion)

2.0 wt % of chrysanthemum extract or 3,5-dicaffeoylquinic acid
3.0 wt % of glycerin
2.0 wt % of butylene glycol
2.0 wt % of propylene glycol
0.1 wt % of carboxy vinyl polymer
0.2 wt % of PEG 12 nonylphenylether
0.4 wt % of polysorbate 80
10.0 wt % of ethanol
0.1 wt % of triethanolamine
Preservative, colorant, flavor q.s.
100 wt % of distilled water Although components relatively suitable for a skin toner were mixed as a preferable example, a mixing ratio may be arbitrarily changed. The skin toner may be prepared by a conventional method used in the cosmetics field.

Preparation Example 10: Preparation of Nourishing Cream 2.0 wt % of chrysanthemum extract or 3,5-dicaffeoylquinic acid
1.5 wt % of polysorbate 60
0.5 wt % of sorbitan sesquioleate
2.0 wt % of PEG60 hydrogenated castor oil
10 wt % of liquid paraffin
5.0 wt % of squalene
5.0 wt % of caprylic/capric triglyceride
5.0 wt % of glycerin
3.0 wt % of butylene glycol
3.0 wt % of propylene glycol
0.2 wt % of triethanolamine
Preservative q.s.
Colorant q.s.
Flavor q.s.
100 wt % of distilled water Although components relatively suitable for a nourishing cream were mixed as a preferable example, a mixing ratio may be arbitrarily changed. The nourishing toner may be prepared by a conventional method used in the cosmetics field.

Preparation Example 11: Preparation of Massage Cream 1.0 wt % of chrysanthemum extract or 3,5-dicaffeoylquinic acid
10.0 wt % of cera
1.5 wt % of polysorbate 60
2.0 wt % of PEG 12 nonylphenylether
0.8 wt % of sorbitan sesquioleate
40.0 wt % of liquid paraffin
5.0 wt % of squalene
4.0 wt % of caprylic/capric triglyceride
5.0 wt % of glycerin
3.0 wt % of butylene glycol
3.0 wt % of propylene glycol
0.2 wt % of triethanolamine
Preservative, colorant, flavor q.s.
100 wt % of distilled water Although components relatively suitable for a massage cream were mixed as a preferable example, a mixing ratio may be arbitrarily changed. The skin toner may be prepared by a conventional method used in the cosmetics field.

Preparation Example 12: Preparation of Pack 1.0 wt % of chrysanthemum extract or 3,5-dicaffeoylquinic acid
13.0 wt % of polyvinyl alcohol
0.2 wt % of sodium carboxymethylcellulose
5.0 wt % of glycerin
0.1 wt % of allantoin
6.0 wt % of ethanol
0.3 wt % of PEG 12 nonylphenylether
0.3 wt % of polysorbate 60
Preservative, colorant, flavor q.s.
100 wt % of distilled water Although components relatively suitable for a pack were mixed as a preferable example, a mixing ratio may be arbitrarily changed. The skin toner may be prepared by a conventional method used in the cosmetics field.

Preparation Example 13: Preparation of Gel 0.5 wt % of chrysanthemum extract or 3,5-dicaffeoylquinic acid
0.05 wt % of ethylenediamine sodium acetate
5.0 wt % of glycerin
0.3 wt % of carboxyvinyl polymer
5.0 wt % of ethanol
0.5 wt % of PEG60 hydrogenated castor oil
0.3 wt % of triethanolamine
Preservative, colorant, flavor q.s.
100 wt % of distilled water Although components relatively suitable for a gel were mixed as a preferable example, a mixing ratio may be arbitrarily changed. The skin toner may be prepared by a conventional method used in the cosmetics field.

Components relatively suitable for a cosmetic composition were mixed as a preferable example, and may also be applied to various types of cosmetics including color cosmetics. The components may be used to prepare a medication to be thinly applied to a human body depending on its efficacy, that is, an ointment, and a mixing ratio may be arbitrarily changed according to regional and national preferences such as the demand level, the country of demand, a purpose of use, etc.

It should be understood by those of ordinary skill in the art that the above description of the present invention is exemplary, and the exemplary embodiments disclosed herein can be easily modified into other specific forms without departing from the technical spirit or essential features of the present invention. Therefore, the exemplary embodiments described above should be interpreted as illustrative and not limited in any aspect.

The invention claimed is:

1. A method of improving muscle function, comprising:
administering a pharmaceutically effective amount of a *Chrysanthemum morifolium* extract, or 3,5-dicaffeoylquinic acid represented by Formula 1 below or a pharmaceutically acceptable salt thereof to a subject:

[Formula 1]

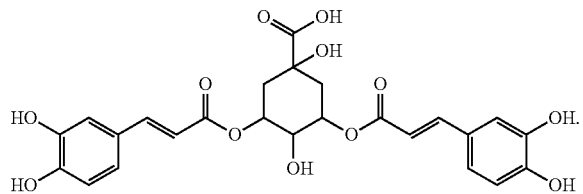

2. The method according to claim 1, wherein the *Chrysanthemum morifolium* extract includes 3,5-dicaffeoylquinic acid represented by Formula 1 below:

[Formula 1]

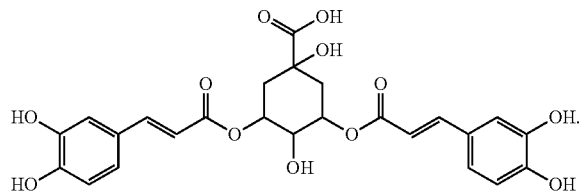

3. The method according to claim 1, wherein the *Chrysanthemum morifolium* extract is obtained by extracting *Chrysanthemum morifolium* using water, an organic solvent having 1 to 6 carbon atoms or a mixture thereof as a solvent.

4. The method according to claim 1, wherein the *Chrysanthemum morifolium* extract is obtained by extracting *Chrysanthemum morifolium* by subcritical fluid extraction, supercritical fluid extraction or ultra-high pressure extraction.

5. The method according to claim 1, wherein the 3,5-dicaffeoylquinic acid is a compound isolated from a *Chrysanthemum morifolium* extract.

* * * * *

SEQUENCE LISTING

<160> NUMBER OF SEQ ID NOS: 12

<210> SEQ ID NO 1
<211> LENGTH: 20
<212> TYPE: DNA
<213> ORGANISM: Artificial sequence
<220> FEATURE:
<223> OTHER INFORMATION: Atrogin-1_PrimerF

<400> SEQUENCE: 1
ccctgagtgg catcgcccaa                                               20

<210> SEQ ID NO 2
<211> LENGTH: 19
<212> TYPE: DNA
<213> ORGANISM: artificial sequence
<220> FEATURE:
<223> OTHER INFORMATION: Atrogin-1_PrimerR

<400> SEQUENCE: 2
aggtcccgcc catcgctca                                                19

<210> SEQ ID NO 3
<211> LENGTH: 20
<212> TYPE: DNA
<213> ORGANISM: artificial sequence
<220> FEATURE:
<223> OTHER INFORMATION: MuRF-1_PrimerF

<400> SEQUENCE: 3
tctactcggc cacaggcgct                                               20

<210> SEQ ID NO 4
<211> LENGTH: 20
<212> TYPE: DNA
<213> ORGANISM: artificial sequence
<220> FEATURE:
<223> OTHER INFORMATION: MuRF-1_PrimerR

<400> SEQUENCE: 4
cttgacagct cccgccgcaa                                               20

<210> SEQ ID NO 5
<211> LENGTH: 20
<212> TYPE: DNA
<213> ORGANISM: artificial sequence
<220> FEATURE:
<223> OTHER INFORMATION: b-actin_PrimerF

<400> SEQUENCE: 5
agccatgtac gtagccatcc                                               20

<210> SEQ ID NO 6
<211> LENGTH: 20
<212> TYPE: DNA
<213> ORGANISM: artificial sequence
<220> FEATURE:
<223> OTHER INFORMATION: b-actin_PrimerR

<400> SEQUENCE: 6
ctctcagctg tggtgctgaa                                               20

<210> SEQ ID NO 7
<211> LENGTH: 20
<212> TYPE: DNA
<213> ORGANISM: artificial sequence

```
<220> FEATURE:
<223> OTHER INFORMATION: MyoD_PrimerF

<400> SEQUENCE: 7
ggatggtgcc cctgggtcct                                              20

<210> SEQ ID NO 8
<211> LENGTH: 20
<212> TYPE: DNA
<213> ORGANISM: artificial sequence
<220> FEATURE:
<223> OTHER INFORMATION: MyoD_PrimerR

<400> SEQUENCE: 8
tggccttcgc tgtgagtcgc                                              20

<210> SEQ ID NO 9
<211> LENGTH: 20
<212> TYPE: DNA
<213> ORGANISM: artificial sequence
<220> FEATURE:
<223> OTHER INFORMATION: myogenin_PrimerF

<400> SEQUENCE: 9
tgggctgcca caagccagac                                              20

<210> SEQ ID NO 10
<211> LENGTH: 20
<212> TYPE: DNA
<213> ORGANISM: artificial sequence
<220> FEATURE:
<223> OTHER INFORMATION: myogenin_PrimerR

<400> SEQUENCE: 10
cagcccagcc actggcatca                                              20

<210> SEQ ID NO 11
<211> LENGTH: 22
<212> TYPE: DNA
<213> ORGANISM: artificial sequence
<220> FEATURE:
<223> OTHER INFORMATION: b-actin_PrimerF

<400> SEQUENCE: 11
ctgtgtggat tggtggctct at                                           22

<210> SEQ ID NO 12
<211> LENGTH: 23
<212> TYPE: DNA
<213> ORGANISM: artificial sequence
<220> FEATURE:
<223> OTHER INFORMATION: b-actin_PrimerR

<400> SEQUENCE: 12
gtgtaaaacg cagctcagta aca                                          23
```